(12) United States Patent
Xue

(10) Patent No.: US 7,072,709 B2
(45) Date of Patent: Jul. 4, 2006

(54) METHOD AND APPARATUS FOR DETERMINING ALTERNANS DATA OF AN ECG SIGNAL

(75) Inventor: Joel Q. Xue, Germantown, WI (US)

(73) Assignee: GE Medical Information Technologies, Inc., Milwaukee, WI (US)

( * ) Notice: Subject to any disclaimer, the term of this patent is extended or adjusted under 35 U.S.C. 154(b) by 75 days.

(21) Appl. No.: 10/825,495

(22) Filed: Apr. 15, 2004

(65) Prior Publication Data

US 2005/0234363 A1 Oct. 20, 2005

(51) Int. Cl.
*A61B 5/0402* (2006.01)

(52) U.S. Cl. ...................................... 600/509; 600/517

(58) Field of Classification Search ........ 600/515–517, 600/509, 512, 513; 128/920, 923
See application file for complete search history.

(56) References Cited

U.S. PATENT DOCUMENTS

| | | |
|---|---|---|
| 3,554,187 A | 1/1971 | Glassner et al. |
| 3,658,055 A | 4/1972 | Abe et al. |
| 3,759,248 A | 9/1973 | Valiquette |
| 3,821,948 A | 7/1974 | King |
| 3,902,479 A | 9/1975 | Chaumet |
| 3,952,731 A | 4/1976 | Worstencroft |
| 4,124,894 A | 11/1978 | Vick et al. |
| 4,136,690 A | 1/1979 | Anderson et al. |
| 4,170,992 A | 10/1979 | Dillman |
| 4,181,135 A | 1/1980 | Andresen et al. |
| 4,202,340 A | 5/1980 | Langer et al. |
| 4,316,249 A | 2/1982 | Gallant et al. |
| 4,417,306 A | 11/1983 | Citron et al. |
| 4,422,459 A | 12/1983 | Simson |
| 4,432,375 A | 2/1984 | Angel et al. |
| 4,457,315 A | 7/1984 | Bennish |
| 4,458,691 A | 7/1984 | Netravali |

(Continued)

FOREIGN PATENT DOCUMENTS

DE 2604460 8/1977

(Continued)

OTHER PUBLICATIONS

Okin et al. "Principal Component Analysis of the T Wave and Prediction of Cardiovascular Mortality in American Indians". 105 Circulation 714 (2002).*

(Continued)

*Primary Examiner*—Robert E. Pezzuto
*Assistant Examiner*—Jessica L. Reidel
(74) *Attorney, Agent, or Firm*—Andrus, Sceales, Starke & Sawall, LLP

(57) ABSTRACT

Method and apparatus for determining alternans data of an ECG signal. The method can include determining at least one value representing at least one morphology feature of each beat of the ECG signal and generating a set of data points based on a total quantity of values and a total quantity of beats. The data points can each include a first value determined using a first mathematical function and a second value determined using a second mathematical function. The method can also include several preprocessing algorithms to improve the signal to noise ratio. The method can also include separating the data points into a first group of points and a second group of points and generating a feature map by plotting the first group of points and the second group of points in order to assess an alternans pattern of variation. The feature map can be analyzed by statistical tests to determine the significance difference between groups and clusters.

15 Claims, 18 Drawing Sheets

U.S. PATENT DOCUMENTS

| | | | |
|---|---|---|---|
| 4,458,692 A | 7/1984 | Simson | |
| 4,475,558 A | 10/1984 | Brock | |
| 4,492,235 A | 1/1985 | Sitrick | |
| 4,519,395 A | 5/1985 | Hrushesky | |
| 4,583,553 A | 4/1986 | Shah et al. | |
| 4,589,420 A | 5/1986 | Adams et al. | |
| 4,603,703 A | 8/1986 | McGill et al. | |
| 4,616,659 A | 10/1986 | Prezas et al. | |
| 4,665,485 A | 5/1987 | Lundy et al. | |
| 4,679,144 A | 7/1987 | Cox et al. | |
| 4,680,708 A | 7/1987 | Ambos et al. | |
| 4,732,157 A | 3/1988 | Kaplan et al. | |
| 4,796,638 A | 1/1989 | Sasaki | |
| 4,802,491 A | 2/1989 | Cohen et al. | |
| 4,832,038 A | 5/1989 | Arai et al. | |
| 4,854,327 A | 8/1989 | Kunig | |
| 4,860,762 A | 8/1989 | Heumann et al. | |
| 4,896,677 A | 1/1990 | Kaneko et al. | |
| 4,924,875 A | 5/1990 | Chamoun | |
| 4,928,690 A | 5/1990 | Heilman et al. | |
| 4,938,228 A | 7/1990 | Righter et al. | |
| 4,951,680 A | 8/1990 | Kirk et al. | |
| 4,955,382 A | 9/1990 | Franz et al. | |
| 4,958,641 A | 9/1990 | Digby et al. | |
| 4,972,834 A | 11/1990 | Begemann et al. | |
| 4,974,162 A | 11/1990 | Siegel et al. | |
| 4,974,598 A | 12/1990 | John | |
| 4,977,899 A | 12/1990 | Digby et al. | |
| 4,979,510 A | 12/1990 | Franz et al. | |
| 4,989,610 A | 2/1991 | Patton et al. | |
| 5,000,189 A | 3/1991 | Throne et al. | |
| 5,010,888 A | 4/1991 | Jadvar et al. | |
| 5,020,540 A | 6/1991 | Chamoun | |
| 5,025,795 A | 6/1991 | Kunig | |
| 5,042,497 A | 8/1991 | Shapland | |
| 5,092,341 A | 3/1992 | Kelen | |
| 5,109,862 A | 5/1992 | Kelen et al. | |
| 5,117,833 A | 6/1992 | Albert et al. | |
| 5,117,834 A | 6/1992 | Kroll et al. | |
| 5,148,812 A | 9/1992 | Verrier et al. | |
| 5,188,116 A | 2/1993 | Pommrehn et al. | |
| 5,201,321 A | 4/1993 | Fulton | |
| 5,234,404 A | 8/1993 | Tuttle et al. | |
| 5,253,650 A | 10/1993 | Wada | |
| 5,265,617 A | 11/1993 | Verrier et al. | |
| 5,277,190 A | 1/1994 | Moulton | |
| 5,323,783 A | 6/1994 | Henkin et al. | |
| 5,343,870 A | 9/1994 | Gallant et al. | |
| 5,423,878 A | 6/1995 | Franz | |
| 5,437,285 A | 8/1995 | Verrier et al. | |
| 5,560,370 A | 10/1996 | Verrier et al. | |
| 5,570,696 A | 11/1996 | Arnold et al. | |
| 5,819,741 A | 10/1998 | Karlsson et al. | |
| 5,891,045 A * | 4/1999 | Albrecht et al. | 600/509 |
| 5,921,940 A | 7/1999 | Verrier et al. | |
| 5,935,082 A | 8/1999 | Albrecht et al. | |
| 6,047,206 A * | 4/2000 | Albrecht et al. | 600/509 |
| 6,169,919 B1 | 1/2001 | Nearing et al. | |
| 6,453,191 B1 | 9/2002 | Krishnamachari | |
| 6,463,320 B1 * | 10/2002 | Xue et al. | 600/523 |
| 6,668,189 B1 | 12/2003 | Kaiser et al. | |
| 6,760,615 B1 * | 7/2004 | Ferek-Petric | 600/518 |
| 2004/0162498 A1 * | 8/2004 | Kaiser et al. | 600/515 |

FOREIGN PATENT DOCUMENTS

| | | |
|---|---|---|
| DE | 3303104 | 8/1984 |
| DE | 4024360 | 3/1991 |
| EP | 0080821 | 6/1983 |
| FR | 2539978 | 8/1984 |
| GB | 2070871 | 9/1981 |
| WO | WO81/02832 | 10/1981 |

OTHER PUBLICATIONS

Speranza et al., 'Beat-to-beat measurement and analysis of the R-T interval in 24 h ECG Holter recordings,' Med and Biol Eng & Comput, 1993, 31, pp. 487-494.

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., 'Holter monitoring in the long QT syndrome of children and adolescents,' Cor Vasa, 1990, 32(6), pp. 474-483.

Vavarro-Lopez et al., 'Isolated T wave alternans elicited by hypocalcemia in dogs,' Electrocardiology, 1978, 11(2), pp. 103-108.

Little et al., 'Torsade de Pointes and T-U wave alternans associated with arsenic poisoning,' Pace, 1990, 13, pp. 164-170

Weintraub et al., 'The congenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after myocardial infarction,' Canadian Journal of Cardiology, Supplement A, Jul. 1986, pp. 71A-84A.

Stroobandt et al., 'Simultaneous recording of atrial and ventricular monophasic action potentials: monophasic action potential duration during atrial pacing, ventricular pacing, and ventricular fibrillation,' Pace, Jul-Aug. 1985, 8, pp. 502-511.

Sharma et al., 'Romano-Ward prolonged QT syndrome with intermittant T wave alternans and atrioventricular block,' American Heart Journal, 1981, pp. 500-501.

Navarro-Lopez et al., 'Isolated T wave alternans,' American Heart Journal, 1978, pp. 369-374.

Mitsutake et al., 'Usefulness of the Valsalva Maneuver in management of the long QT syndrome,' Circulation, 1981, 63(5), pp. 1029-1035.

Nearing et al., 'Personal computer system for tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of its relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability to ventricular fibrillation,' Journal of Cardiovascular Electrophysiology, May 1994, 5(5), pp. 445-461.

Verrier et al., 'Behavioral states and sudden cardiac death,' Pace, Sep. 1992, 15, pp. 1387-1393.

Turitto et al., 'Alternans of the ST segment in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induced ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

* cited by examiner

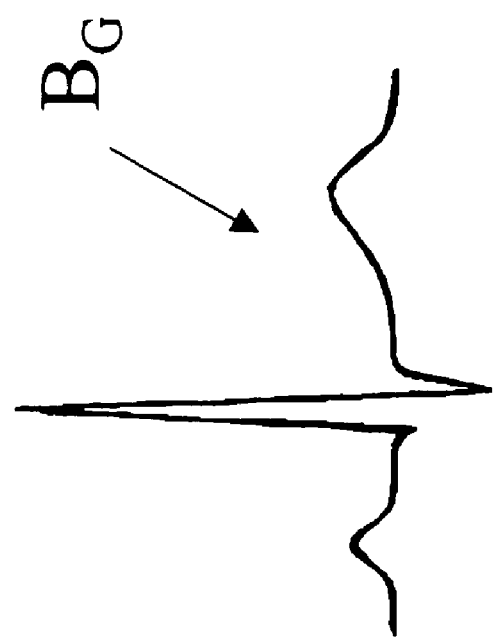
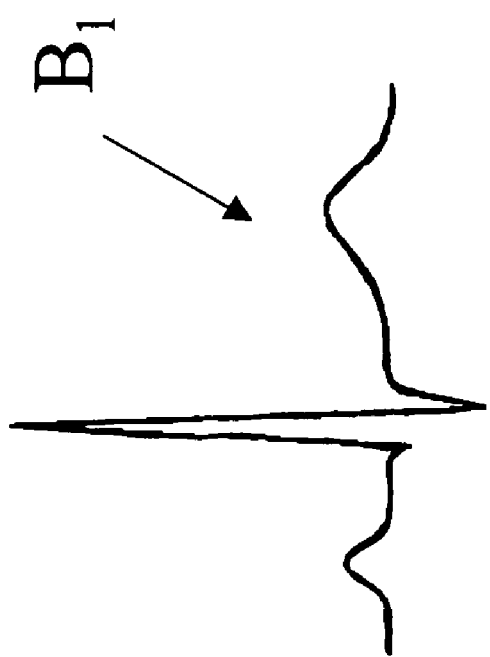
FIG. 2

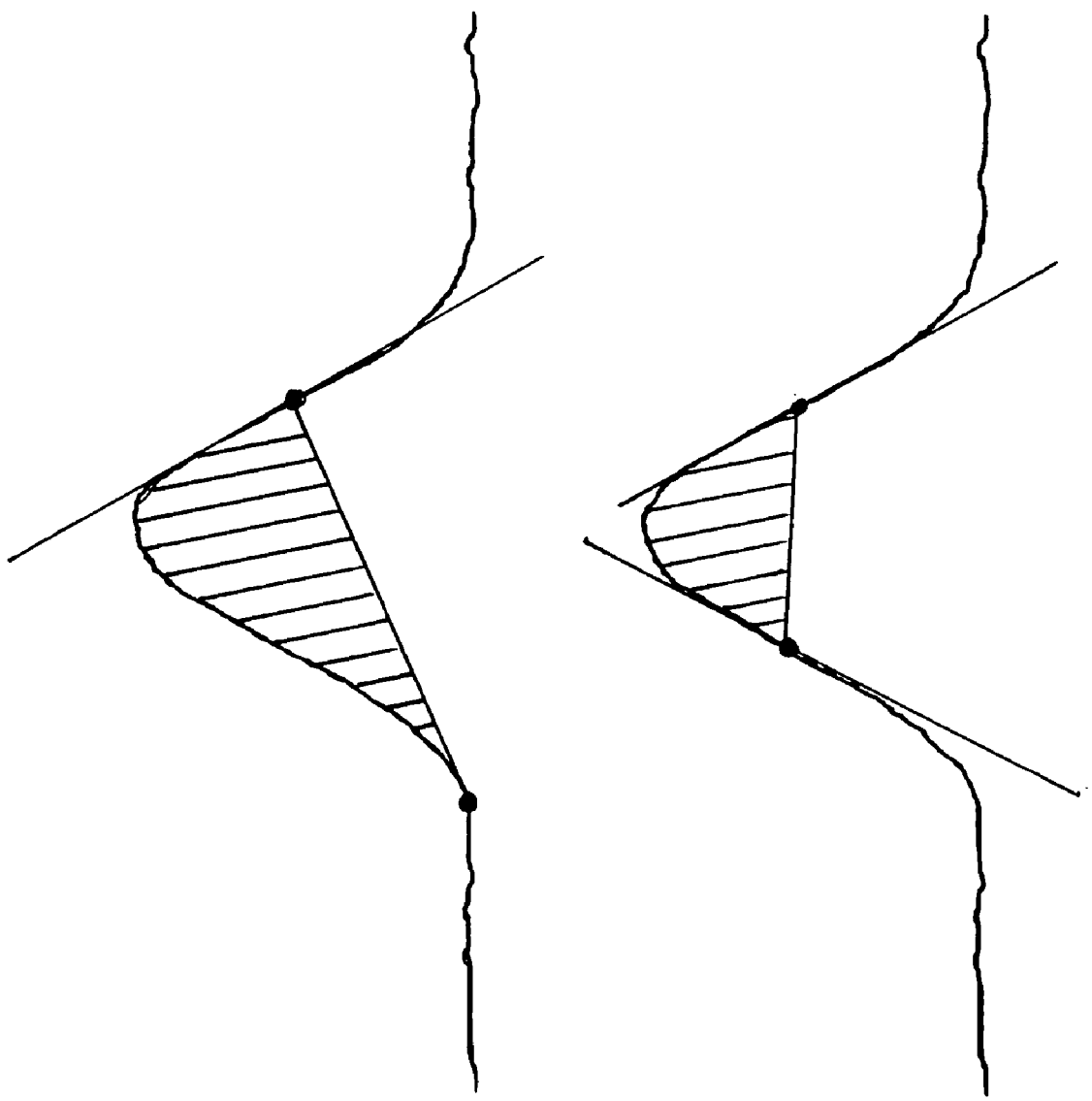

$$A = \begin{bmatrix} W_{1B_1} & W_{2B_1} & \cdots & W_{CB_1} \\ W_{1B_2} & \cdots & \cdots & \cdots \\ \vdots & \vdots & \vdots & \vdots \\ W_{1B_H} & \cdots & \cdots & W_{CB_H} \end{bmatrix} = \begin{bmatrix} F_1B_1 & F_2B_1 & \cdots & F_DB_1 \\ F_1B_2 & \cdots & \cdots & \cdots \\ \vdots & \vdots & \vdots & \vdots \\ F_1B_H & \cdots & \cdots & F_DB_H \end{bmatrix}$$

FIG. 12

$$A = USV^T = [u_1, u_2, \ldots, u_p] \begin{bmatrix} s_1 & 0 & \cdots & 0 \\ 0 & s_2 & & \vdots \\ \vdots & & \ddots & \\ 0 & \cdots & & s_p \end{bmatrix} [v_1, v_2, \ldots, v_p]^T$$

FIG. 13

METHOD AND APPARATUS FOR DETERMINING ALTERNANS DATA OF AN ECG SIGNAL

BACKGROUND OF THE INVENTION

The present invention relates to cardiology, and more specifically to methods and apparatus for determining alternans data of an electrocardiogram ("ECG") signal.

Alternans are a subtle beat-to-beat change in the repeating pattern of an ECG signal. Several studies have demonstrated a high correlation between an individual's susceptibility to ventricular arrhythmia and sudden cardiac death and the presence of a T-wave alternans ("TWA") pattern of variation in the individual's ECG signal.

While an ECG signal typically has an amplitude measured in millivolts, an alternans pattern of variation with an amplitude on the order of a microvolt may be clinically significant. Accordingly, an alternans pattern of variation is typically too small to be detected by visual inspection of the ECG signal in its typical recorded resolution. Instead, digital signal processing and quantification of the alternans pattern of variation is necessary. Such signal processing and quantification of the alternans pattern of variation is complicated by the presence of noise and time shift of the alternans pattern of variation to the alignment points of each beat, which can be caused by limitation of alignment accuracy and/or physiological variations in the measured ECG signal. Current signal processing techniques utilized to detect TWA patterns of variation in an ECG signal include spectral domain methods and time domain methods.

BRIEF DESCRIPTION OF THE INVENTION

In light of the above, a need exists for a technique for detecting TWA patterns of variation in an ECG signal that provides improved performance as a stand-alone technique and as an add-on to other techniques. Accordingly, one or more embodiments of the invention provide methods and apparatus for determining alternans data of an ECG signal. In some embodiments, the method can include determining at least one value representing at least one morphology feature of each beat of the ECG signal and generating a set of data points based on a total quantity of values and a total quantity of beats. The data points can each include a first value determined using a first mathematical function and a second value determined using a second mathematical function. The method can also include separating the data points into a first group of points and a second group of points and generating a feature map by plotting the first group of points and the second group of points in order to assess an alternans pattern of variation.

DESCRIPTION OF THE DRAWINGS

FIG. 2 illustrates an ECG signal.

FIG. 8 illustrates a further area morphology feature.

FIG. 9 illustrates still another area morphology feature.

FIG. 12 illustrates a feature matrix.

FIG. 13 illustrates a decomposition of the feature matrix of FIG. 12 as generated by a principal component analysis.

DETAILED DESCRIPTION

Figure 1:
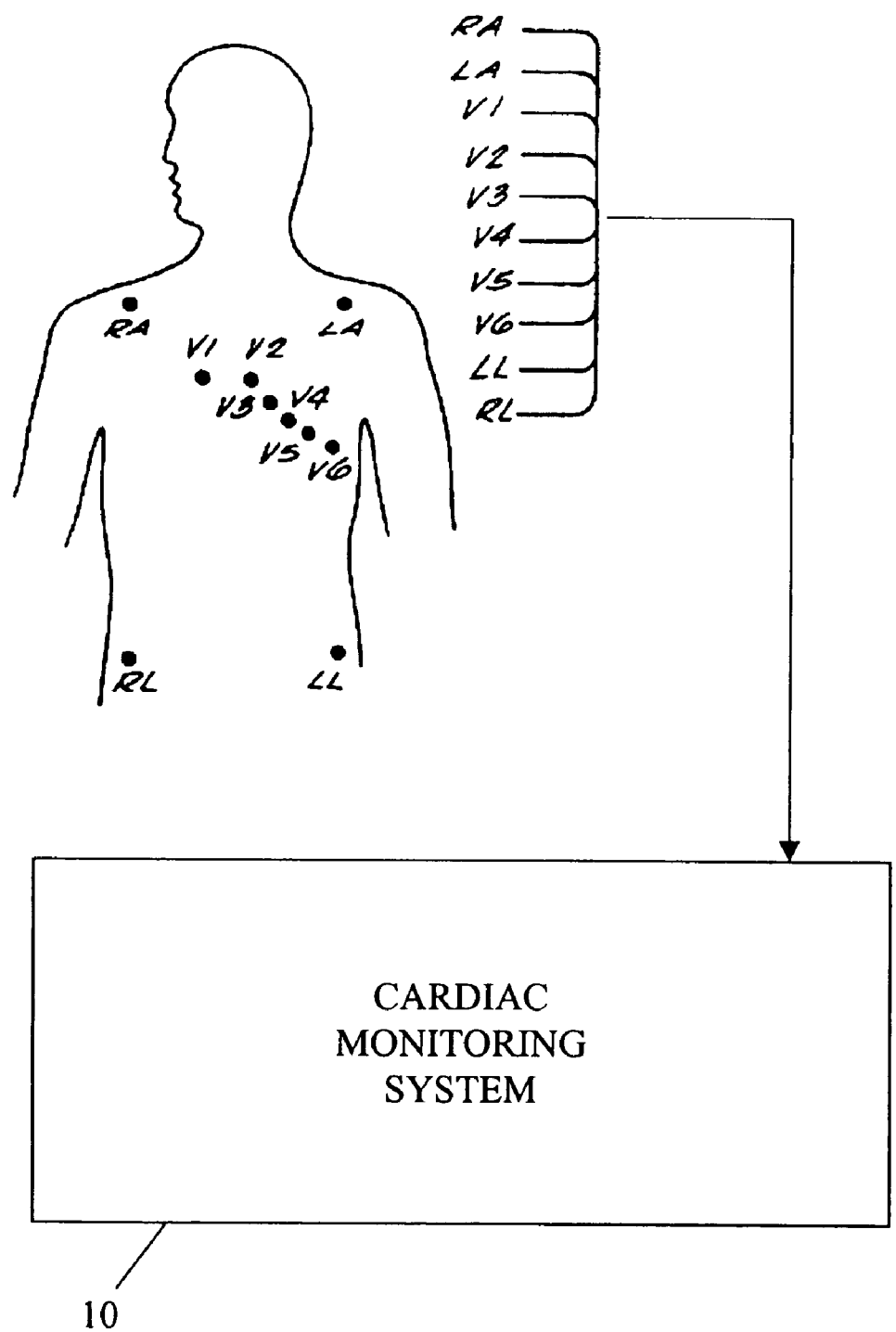
FIG. 1 is a schematic diagram illustrating a cardiac monitoring system according to the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a cardiac monitoring system 10 according to some embodiments of the invention. The cardiac monitoring system 10 can acquire ECG data, can process the acquired ECG data to determine alternans data, and can output the alternans data to a suitable output device (e.g., a display, a printer, and the like). As used herein and in the appended claims, the term "alternans data" includes TWA data, or any other type of alternans data that is capable of being determined using one or more embodiments of the invention.

The cardiac monitoring system 10 can acquire ECG data using a data acquisition module. It should be understood that ECG data can be acquired from other sources (e.g., from storage in a memory device or a hospital information system). The data acquisition module can be coupled to a patient by an array of sensors or transducers which may include, for example, electrodes coupled to the patient for obtaining an ECG signal. In the illustrated embodiment, the electrodes can include a right arm electrode RA; a left arm electrode LA; chest electrodes V1, V2, V3, V4, V5 and V6; a right leg electrode RL; and a left electrode leg LL for acquiring a standard twelve-lead, ten-electrode ECG. In other embodiments, alternative configurations of sensors or transducers (e.g., less than ten electrodes) can be used to acquire a standard or non-standard ECG signal.

A representative ECG signal is schematically illustrated in FIG. 2. The ECG signal can include [G] beats including beat-one $B_1$ through beat-[G] $B_G$ where [G] is a value greater than one. As used herein and in the appended claims, a capital letter in brackets represents a quantity, and a capital letter without brackets is a reference character (similar to a typical reference numeral).

The data acquisition module can include filtering and digitization components for producing digitized ECG data representing the ECG signal. In some embodiments, the ECG data can be filtered using low pass and baseline wander removal filters to remove high frequency noise and low frequency artifacts. The ECG data can, in some embodiments, be filtered by removing arrhythmic beats from the ECG data and by eliminating noisy beats from the ECG data.

Figure 3:
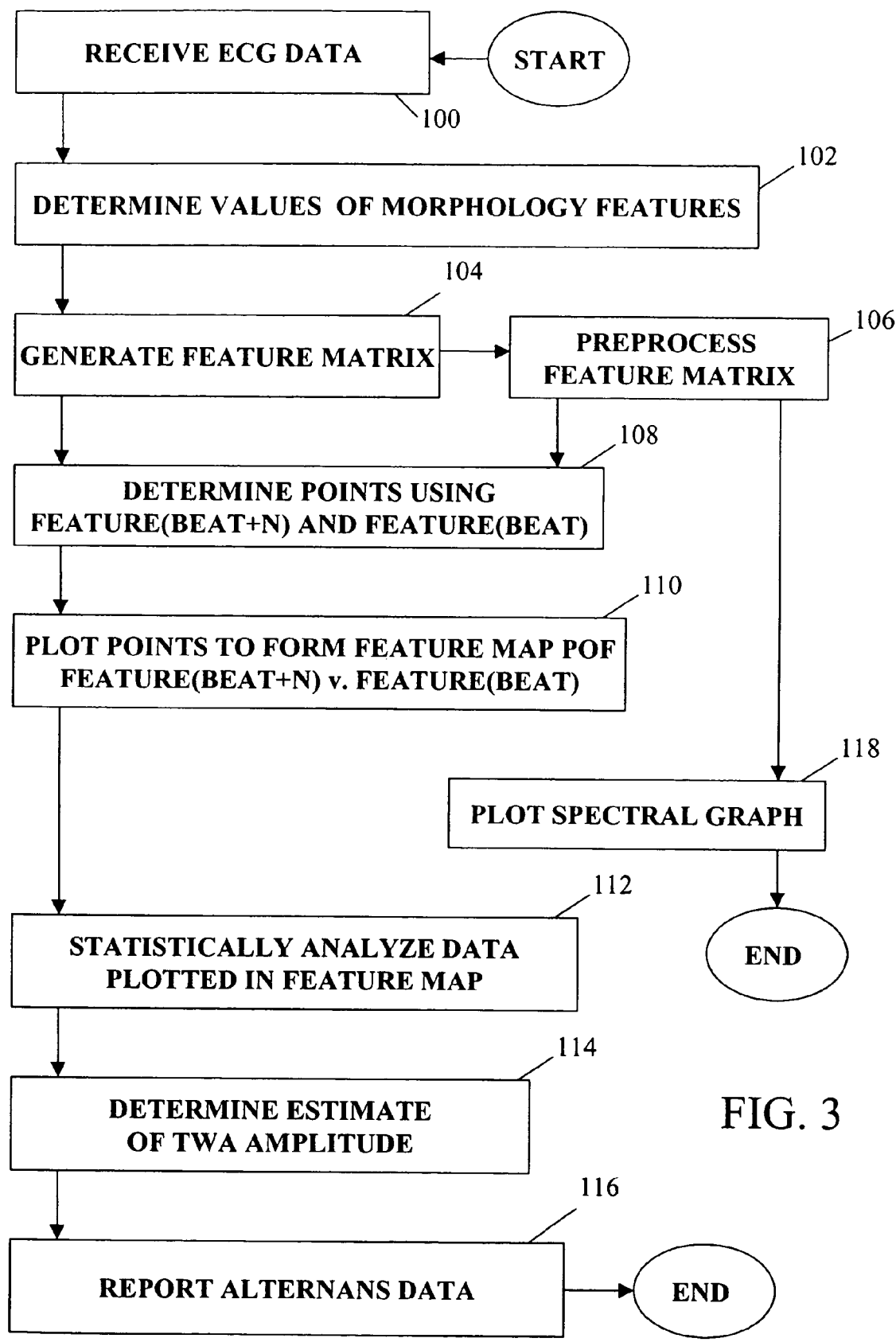
FIG. 3 is a flow chart illustrating one embodiment of a method of the invention.

The cardiac monitoring system 10 can include a processor and a memory associated with the processor. The processor can execute a software program stored in the memory to perform a method of the invention as illustrated in FIG. 3. FIG. 3 is a flow chart of a method of the invention used to determine and display alternans data of an ECG signal. Although the cardiac monitoring system 10 is described herein as including a single processor that executes a single software program, it should be understood that the system can include multiple processors, memories, and/or software programs. Further, the method of the invention illustrated in FIG. 3 can be performed manually or using other systems.

As shown in FIG. 3, the processor can receive (at 100) ECG data representing an ECG signal. The acquired ECG data can be received (e.g., from a patient in real-time via the data acquisition module or from storage in a memory device) and can be processed as necessary. The ECG data can represent continuous and/or non-continuous beats of the ECG signal. In one embodiment, the ECG data, or a portion thereof, can be parsed into a plurality of data sets. Each data set can represent a portion of a respective beat B of the ECG signal (e.g., the T-wave portion of a respective beat B of the ECG signal), a portion of a respective odd or even median beat of the ECG signal, a portion of a respective odd or even mean beat of the ECG signal, and the like. The parsed data sets can be saved in an array (e.g., a waveform array). In other embodiments, the ECG data can be saved in a single data set, or alternatively, saved in multiple data sets.

The processor can determine (at 102) a quantity [C] of values W representing a quantity [D] of morphology features F of a beat B (e.g., beat-one $B_1$) of a quantity [G] beats, where [C] and [D] are each a quantity greater than or equal to one. In some embodiments, a single value W is determined for each morphology feature F (i.e., the quantity of [C] is equal to the quantity of [D]). However, in some embodiments, multiple values W are determined for a single morphology feature F and/or a single value W is determined for multiple morphology features F. Determining a quantity [C] of values W representing a quantity [D] of morphology features F can be repeated for a quantity [H−1] of beats of the quantity [G] of beats represented in the collected ECG data where a quantity [H] is greater than or equal to one and less than or equal to the quantity [G].

Figures 4, 5:
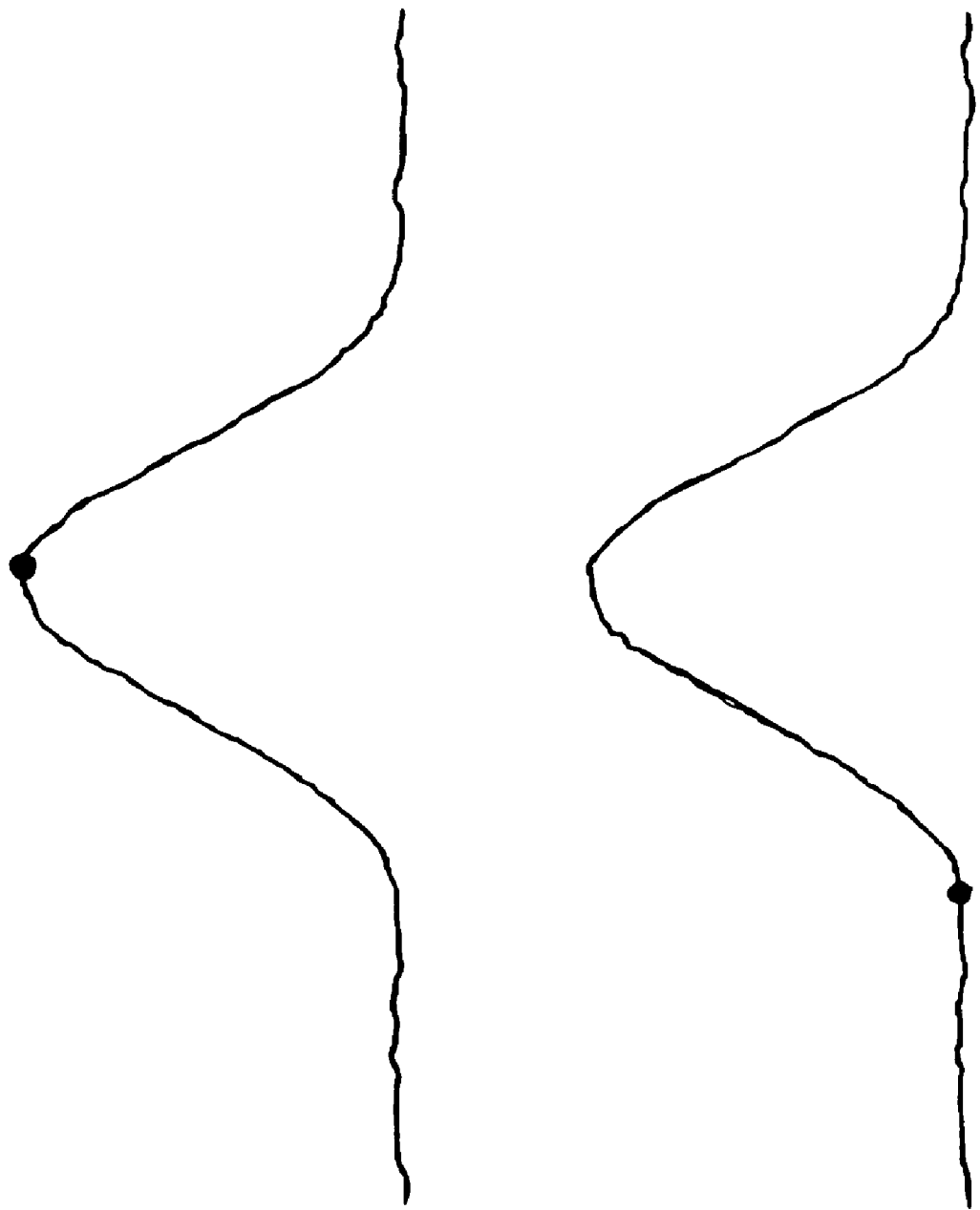
FIG. 4 illustrates a maximum morphology feature.
FIG. 5 illustrates a minimum morphology feature.
Figures 6, 7:
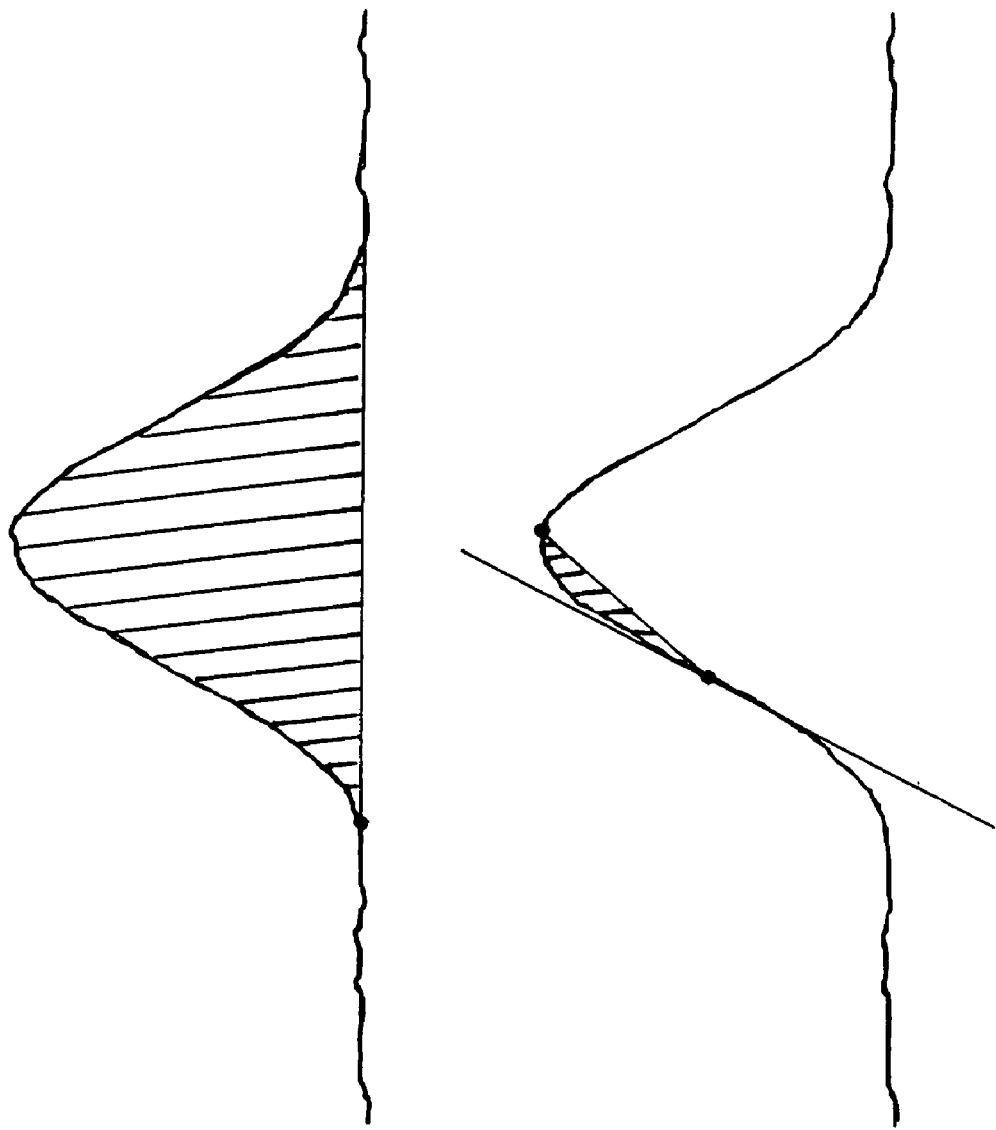
FIG. 6 illustrates an area morphology feature.
FIG. 7 illustrates another area morphology feature.

In some embodiments, any morphology features F of the beats B can be determined. FIGS. 4–9 illustrate some examples of such morphology features F. FIG. 4 illustrates a maximum morphology feature (i.e., the maximum value of the data set representing the T-wave portion of a respective beat). FIG. 5 illustrates a minimum morphology feature (i.e., the minimum value of the data set representing the T-wave portion of a respective beat). FIG. 6 illustrates an area morphology feature (i.e., the area between a curve formed by the data set representing the T-wave portion of a respective beat and a baseline established by the minimum value of the data set). FIG. 7 illustrates another area morphology feature (i.e., the area between a curve formed by the data set representing the T-wave portion of a respective beat and a baseline established by the maximum value of the data set and a point of the data set representing the maximum up-slope of the curve). FIG. 8 illustrates still another area morphology feature (i.e., the area between a curve formed by the data set representing the T-wave portion of a respective beat and a baseline established by the minimum value of the data set and a point of the data set representing the maximum down-slope of the curve). FIG. 9 illustrates yet another area morphology feature (i.e., the area between a curve formed by the data set representing the T-wave portion of a respective beat and a baseline established by a point of the data set representing the maximum up-slope of the curve and a point of the data set representing the maximum down-slope of the curve). Other types of maximum, minimum, and area morphology features can also be used.

Other examples of morphology features that can be used include amplitude morphology features (e.g., an amplitude of a point representing the maximum down-slope of the curve formed by the data set representing the T-wave portion of a respective beat) and slope morphology features (e.g., a maximum positive slope of the curve formed by the data set representing the T-wave portion of a respective beat). Another example is mathematical model morphology features obtained by determining values representing a mathematical model of the curve formed by the data set representing the T-wave portion of a respective beat using, for example, a Gaussian function model, a power of Cosine function model, and/or a bell function model. A further example is time interval morphology features (e.g., a time interval between a maximum value and a minimum value of the data set representing a T-wave portion of a respective beat). Still another example is shape correlation morphology features obtained by determining a value representing a shape correlation of the curve formed by the data set representing the T-wave portion of a respective beat using, for example, a cross-correlation method and/or an absolute difference correlation method. An additional example is ratio morphology features (e.g., a ST:T ratio). Any other suitable morphology feature can be used in other embodiments of the invention. In some embodiments, as discussed above, the morphology feature can be determined using values of the data set(s) of the ECG data. In other embodiments, the morphology features can be determined using values representing the values of the data set(s) of the ECG data (e.g., a morphology feature of the first derivative of the curve formed by a respective data set).

Figure 10:
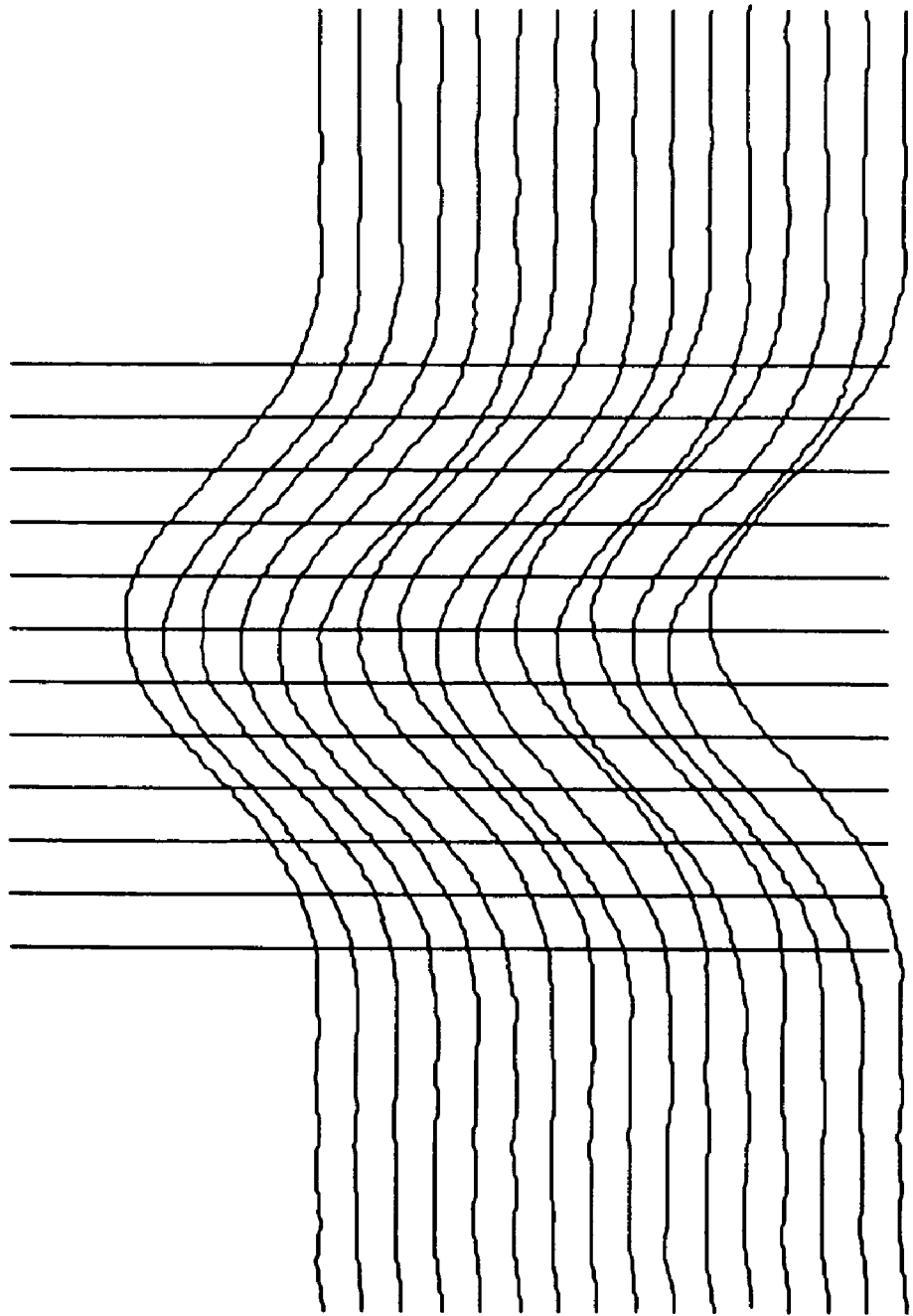
FIG. 10 illustrates a plurality of beats, each beat being divided into a plurality of portions.
Figure 11:
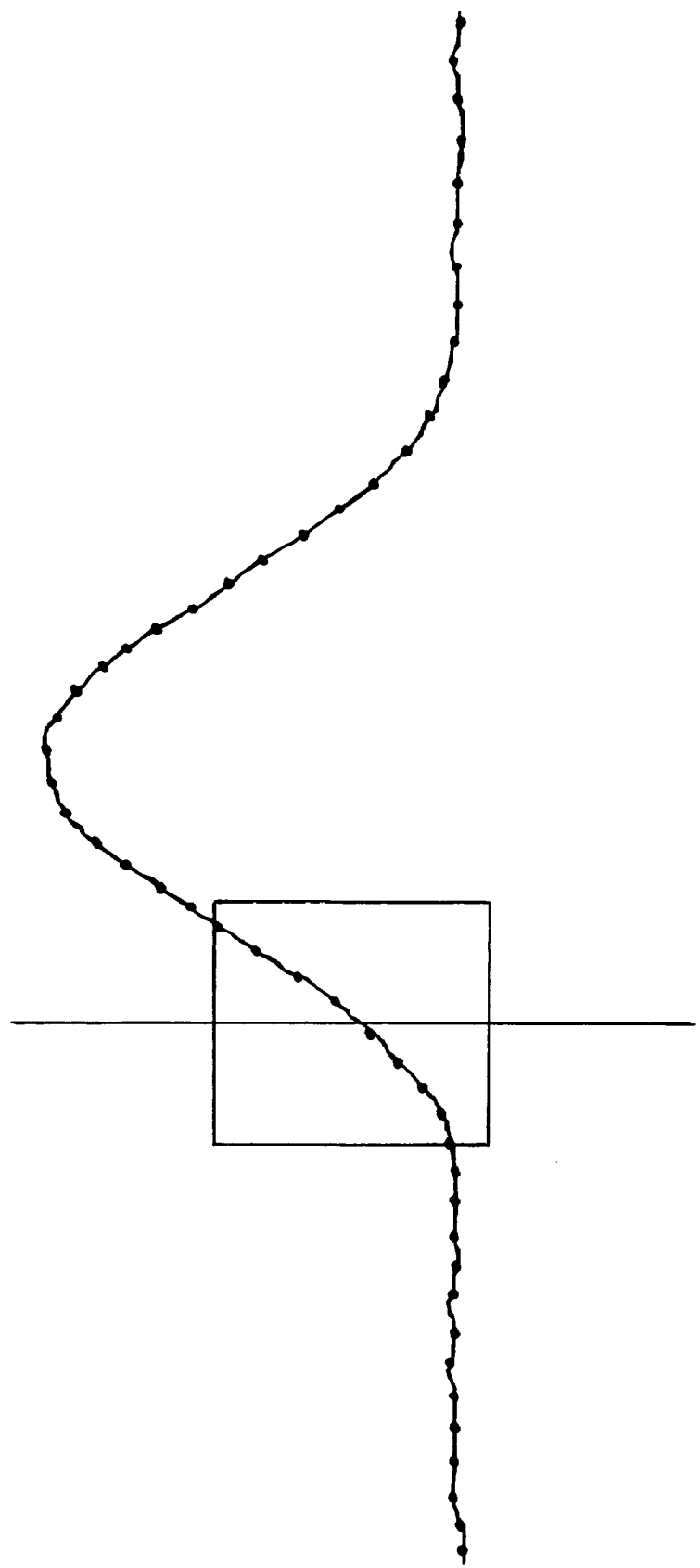
FIG. 11 illustrates a window establishing a size of one of the plurality of portions of FIG. 10.

Morphology features can be determined using an entire parsed data set as illustrated in FIGS. 4–9, or alternatively, using a portion thereof as illustrated in FIGS. 10 and 11. As shown in FIG. 10, each of the beats B can be divided up in a plurality of portions. The center of each portion can be defined by a vertical divider line. As shown in FIG. 11, a window can be established to define the size of the portion. The window can include a single value of the data set (e.g., a value representing the point where the divider line crosses the curve formed by the data set), or values of the data set representing any number of points adjacent the intersection of the curve and the divider line.

As shown in FIG. 3, the processor can generate (at 104) a feature matrix. As used herein and in the appended claims, the term "matrix" includes any table of values. The generated feature matrix can include a quantity [C] of values W representing each of the quantity [D] of morphology features F for each of the quantity [H] of beats B (i.e., the feature matrix includes a quantity [C]×[H] of values W). Each value W can directly represent the determined morphology feature F (e.g., the actual value of the determined area morphology feature), or can indirectly represent the determined morphology feature (e.g., a normalized value of the determined area morphology feature).

A representative column-wise feature matrix A is illustrated in FIG. 12. The feature matrix A can include [C] columns and [H] rows. The feature matrix A can use the columns to represent the quantity [D] of morphology features F (i.e., each column includes a quantity [H] of values W of the same morphology feature as determined for each of the quantity [H] of beats B), and the rows to represent the beats B (i.e., each row includes a quantity [C] of values representing the quantity [D] of morphology features for each of the quantity [H] of beats). The values W of the morphology features F can be represented in the illustrated feature matrix A using the notation $W_{I B_J}$ and $F_I B_J$ where I is a value between one and [C], the quantity of [C] being equal to the quantity of [D], and J is a value between one and [H]. In other embodiments, the feature matrix A can be arranged in other suitable manners. In yet other embodiments, the values W representing the morphology features F can be saved for later processing.

As shown in FIG. 3, the processor can preprocess (at 106) the feature matrix A. In some embodiments, a principal component analysis (PCA) can be performed on the feature matrix A. PCA involves a multivariate mathematical procedure known as an eigen analysis which rotates the data to maximize the explained variance of the feature matrix A. In other words, a set of correlated variables are transformed into a set of uncorrelated variables which are ordered by reducing variability, the uncorrelated variables being linear combinations of the original variables. PCA is used to decompose the feature matrix A into three matrices, as illustrated in FIG. 13. The three matrices can include a matrix U, a matrix S, and a matrix V.

The matrix U can include the principal component vectors (e.g., the first principal component vector $u_1$, the second principal component vector $u_2$, . . . , the pth principal component vector $u_p$). The principal component vectors are also known as eigen vectors. The first principal component vector $u_1$ can represent the most dominant variance vector (i.e., the first principal component vector $u_1$ represents the largest beat-to-beat variance), the second principal component vector $u_2$ can represent the second most dominant variance vector, and so on.

The S Matrix can include the principal components (e.g., the first principal component $S_1$, the second principal component $S_2$, . . . , the pth principal component Sp). The first principal component $S_1$ can account for as much of the variability in the data as possible, and each succeeding principal component S can account for as much of the remaining variability as possible. The first principal component $S_1$ can be used to determine alternans data (e.g., the square-root of the first PCA component $S_1$ can provide an estimation of the amplitude of the most dominant alternans pattern of variation). In some embodiments, the second principal component $S_2$ and the third principal component $S_3$ can also provide useful alternans data.

The matrix V is generally known as the parameter matrix. The matrix V can be raised to a power of T. In other embodiments, the preprocessing of the feature matrix A can include other types of mathematical analyses.

The robustness of the preprocessing of the feature matrix A can be enhanced by increasing the quantity of [H] as the quantity of [D] increases. In other words, an increase in the number of morphology features F represented in the feature matrix A generally requires a corresponding increase in the number of beats B for which the morphology features F are being determined. The correspondence between the quantities of [D] and [H] is often based on the dependency between each of the [D] morphology features F. In some embodiments, the quantity of [H] is greater than or equal to 32 and less than or equal to 128. In other embodiments, the quantity of [H] is less than 32 or greater than 128. In some embodiments, the value of [H] is adaptively changed in response to a corresponding change in the level of noise in the measured ECG signal.

As shown in FIG. 3, the processor can determine (at 108) [E] points L using data corresponding to at least some of the values W, [E] being a quantity greater than or equal to one. The data corresponding to the values W can include at least one value W, at least one value of a principal component vector (e.g., the first principal component vector $u_I$), and/or at least one value of any other data that corresponds to the values W. Each point L can include a first value (e.g., one of an X-value and a Y-value) determined using a first mathematical function Feature(beat+[N]), and a second value (e.g., the other of the X-value and the Y-value) determined using a second mathematical function Feature(beat), [N] being a quantity greater than or equal to one. Each of the first and second values of the points L represents a feature of the data corresponding to the values W. In the illustrated embodiment, the feature is a difference feature Q (i.e., the difference in amplitude between two values of the data corresponding to the values W as specified by the respective mathematical function). In other embodiments, the first and second values of the points L can represent another difference features (e.g., an absolute difference feature, a normalized difference feature, a square-root difference feature, and the like), or any other mathematically-definable feature of the data corresponding to the values W. For example, the feature can include a value feature where the feature is equal to a specified value of the data corresponding to the determined values W.

Equations 1 and 2 shown below define an example of the mathematical functions Feature(beat+[N]) and Feature(beat), respectively. The first values of the points L determined using the mathematical function Feature(beat+[N]) can represent a difference feature $Q_{K+[N]}$ and the second values of the points L determined using the mathematical function Feature(beat) can represent the difference feature $Q_K$, where K is a value equal to a beat (i.e., the beat for which the respective mathematical function is being used to determine either the first or second value of a point L).

$$\text{Feature(beat+}[N])=W_{(beat+2[N])}-W_{(beat+[N])}=Q_{K+[N]} \quad [e1]$$

$$\text{Feature(beat)}=W_{(beat+[N])}-W_{(beat)}=Q_K \quad [e2]$$

Tables 1–3 shown below represent the determination of points L using the mathematical functions Feature(beat+[N]) and Feature(beat) as defined in Equations 1 and 2 for [N]=1, 2, and 3, respectively. Equations 3 and 4 shown below define the mathematical functions Feature(beat+[N]) and Feature(beat) for [N]=1.

$$\text{Feature(beat+1)}=W_{(beat+2)}-W_{(beat+1)}=Q_{K+1} \quad [e3]$$

$$\text{Feature(beat)}=W_{(beat+1)}-W_{(beat)}=Q_K \quad [e4]$$

Equations 5 and 6 shown below define the mathematical functions Feature(beat+[N]) and Feature(beat) for [N]=2.

$$\text{Feature(beat+2)}=W_{(beat+4)}-W_{(beat+2)}=Q_{K+2} \quad [e5]$$

$$\text{Feature(beat)}=W_{(beat+2)}-W_{(beat)}=Q_K \quad [e6]$$

Equations 7 and 8 shown below define the mathematical functions Feature(beat+[N]) and Feature(beat) for [N]=3.

$$\text{Feature(beat+3)}=W_{(beat+6)}-W_{(beat+3)}=Q_{K+3} \quad [e7]$$

$$\text{Feature(beat)}=W_{(beat+3)}-W_{(beat)}=Q_K \quad [e8]$$

As shown by Equations 3–8, the offset between the difference feature $Q_{K+[N]}$ and the difference feature $Q_K$ is dependent on the value of [N]. For [N]=1, the first value of the point L is determined by finding the difference between the value W of the second next beat $B_{1+2}$ and the value W of the next beat $B_{1+1}$, while the second value of the point L is determined by finding the difference between the value W of the next beat $B_{1+1}$ and the value W of the current beat $B_1$. For [N]=2, the first value of the point L is determined by finding the difference between the value W of the fourth next beat $B_{1+4}$ and the value W of the second next beat $B_{1+2}$, while the second value of the point L is determined by finding the difference between the value W of the second next beat $B_{1+2}$ and the value W of the current beat $B_1$. For [N]=3, the first value of the point L is determined by finding the difference between the value W of the sixth next beat $B_{1+6}$ and the value W of the third next beat $B_{1+3}$, while the second value of the point L is determined by finding the difference between the value W of the third next beat $B_{1+3}$ and the value W of the current beat $B_1$. Accordingly, the first values of the points L determined using the first mathematical function Feature(beat+[N]) are offset relative to the second values of the points L determined using the second mathematical function Feature(beat) by a factor of [N]. For example, for [N]=1, the first mathematical function Feature(beat+[N]) determines Feature(2) . . . Feature(Z+1) for beat-one $B_1$ through beat-(Z) $B_Z$, while the second mathematical function Feature(beat) determines Feature(1) . . . Feature(Z) for beat-one $B_1$ through beat-(Z) $B_Z$; for [N]=2, the first mathematical function Feature(beat+[N]) determines Feature(3) . . . Feature(Z+2) for beat-one $B_1$ through beat-(Z) Bz, while the second mathematical function Feature(beat) determines Feature(1) . . . Feature(Z) for beat-one $B_1$ through beat-(Z) $B_Z$; for [N]=3, the first mathematical function Feature(beat+[N]) determines Feature(4) . . . Feature(Z+3) for beat-one $B_1$ through beat-(Z) $B_Z$ while the second mathematical function Feature(beat) determines Feature(1) . . . Feature(Z) for beat-one $B_1$ through beat-(Z) $B_Z$. This offset relationship between the first values of the points L determined using the first mathematical function Feature(beat+[N]) and the second values of the points L determined using the second mathematical function Feature(beat) is further illustrated in Tables 1–3.

In Tables 1–3 shown below, the "Beat" column can represent respective beats B of the ECG signal and the "Feature Value" column can represent a value W of a morphology feature F of the corresponding respective beat B (e.g., an area morphology feature). As discussed above, the points L can be generated using values of other data corresponding to the determined values W. Also in Tables 1–3, an asterisk (*) represents an undetermined value of the point L (i.e., a value of the point L for which feature values W corresponding to beats B subsequent to the listed beats $B_1$-$B_{12}$ are required to determine the value of the point L), "f(b+N)" represents the mathematical function Feature(beat+[N]), and "f(b)" represent the mathematical function Feature(beat). Each point L shown in Tables 1–3 includes an X-value determined using the first mathematical function Feature(beat+[N]) and a Y-value determined using the second mathematical function Feature(beat).

[t1]

[N] = 1

| Beat | Feature Value | f(b + N) = $W_{(b+2N)}$ − $W_{(b+N)}$<br>f(b + 1) = $W_{(b+2)}$ − $W_{(b+1)}$ | f(b) = $W_{(b+N)}$ − $W_{(b)}$<br>f(b) = $W_{(b+1)}$ − $W_{(b)}$ | Feature Map Point | Group |
|---|---|---|---|---|---|
| 1 | 2 | f(2) = 3 − 5 = −2 | f(1) = 5 − 2 = 3 | (−2, 3) | A |
| 2 | 5 | f(3) = 6 − 3 = 3 | f(2) = 3 − 5 = −2 | (3, −2) | B |
| 3 | 3 | f(4) = 2 − 6 = −4 | f(3) = 6 − 3 = 3 | (−4, 3) | A |
| 4 | 6 | f(5) = 4 − 2 = 2 | f(4) = 2 − 6 = −4 | (2, −4) | B |

-continued

[t1]

[N] = 1

| Beat | Value | Feature $f(b + N) = W_{(b+2N)} - W_{(b+N)}$ $f(b + 1) = W_{(b+2)} - W_{(b+1)}$ | $f(b) = W_{(b+N)} - W_{(b)}$ $f(b) = W_{(b+1)} - W_{(b)}$ | Feature Map Point | Group |
|---|---|---|---|---|---|
| 5 | 2 | $f(6) = 3 - 4 = -1$ | $f(5) = 4 - 2 = 2$ | $(-1, 2)$ | A |
| 6 | 4 | $f(7) = 7 - 3 = 4$ | $f(6) = 3 - 4 = -1$ | $(4, -1)$ | B |
| 7 | 3 | $f(8) = 3 - 7 = -4$ | $f(7) = 7 - 3 = 4$ | $(-4, 4)$ | A |
| 8 | 7 | $f(9) = 5 - 3 = 2$ | $f(8) = 3 - 7 = -4$ | $(2, -4)$ | B |
| 9 | 3 | $f(10) = 3 - 5 = -2$ | $f(9) = 5 - 3 = 2$ | $(-2, 2)$ | A |
| 10 | 5 | $f(11) = 7 - 3 = 4$ | $f(10) = 3 - 5 = -2$ | $(4, -2)$ | B |
| 11 | 3 | $f(12) = W_{13} - 7 = *$ | $f(11) = 7 - 3 = 4$ | $(*, 4)$ | A |
| 12 | 7 | $f(13) = W_{14} - W_{13} = *$ | $f(12) = W_{13} - 7 = *$ | $(*, *)$ | B |

[t2]

[N] = 2

| Beat | Value | Feature $f(b + N) = W_{(b+2N)} - W_{(b+N)}$ $f(b + 2) = W_{(b+4)} - W_{(b+2)}$ | $f(b) = W_{(b+N)} - W_{(b)}$ $f(b) = W_{(b+2)} - W_{(b)}$ | Feature Map Point | Group |
|---|---|---|---|---|---|
| 1 | 2 | $f(3) = 2 - 3 = -1$ | $f(1) = 3 - 2 = 1$ | $(-1, 1)$ | A |
| 2 | 5 | $f(4) = 4 - 6 = -2$ | $f(2) = 6 - 5 = 1$ | $(-2, 1)$ | B |
| 3 | 3 | $f(5) = 3 - 2 = 1$ | $f(3) = 2 - 3 = -1$ | $(1, -1)$ | A |
| 4 | 6 | $f(6) = 7 - 4 = 3$ | $f(4) = 4 - 6 = -2$ | $(3, -2)$ | B |
| 5 | 2 | $f(7) = 3 - 3 = 0$ | $f(5) = 3 - 2 = 1$ | $(0, 1)$ | A |
| 6 | 4 | $f(8) = 5 - 7 = -2$ | $f(6) = 7 - 4 = 3$ | $(-2, 3)$ | B |
| 7 | 3 | $f(9) = 3 - 3 = 0$ | $f(7) = 3 - 3 = 0$ | $(0, 0)$ | A |
| 8 | 7 | $f(10) = 7 - 5 = 2$ | $f(8) = 5 - 7 = -2$ | $(2, -2)$ | B |
| 9 | 3 | $f(11) = W_{13} - 3 = *$ | $f(9) = 3 - 3 = 0$ | $(*, *)$ | A |
| 10 | 5 | $f(12) = W_{14} - 7 = *$ | $f(10) = 7 - 5 = 2$ | $(*, *)$ | B |
| 11 | 3 | $f(13) = W_{15} - W_{13} = *$ | $f(11) = W_{13} - 3 = *$ | $(*, *)$ | A |
| 12 | 7 | $f(14) = W_{16} - W_{14} = *$ | $f(12) = W_{14} - 7 = *$ | $(*, *)$ | B |

[t3]

[N] = 3

| Beat | Value | Feature $f(b + N) = W_{(b+2N)} - W_{(b+N)}$ $f(b + 3) = W_{(b+6)} - W_{(b+3)}$ | $f(b) = W_{(b+N)} - W_{(b)}$ $f(b) = W_{(b+3)} - W_{(b)}$ | Feature Map Point | Group |
|---|---|---|---|---|---|
| 1 | 2 | $f(4) = 3 - 6 = -3$ | $f(1) = 6 - 2 = 4$ | $(-3, 4)$ | A |
| 2 | 5 | $f(5) = 7 - 2 = 5$ | $f(2) = 2 - 5 = -3$ | $(5, -3)$ | B |
| 3 | 3 | $f(6) = 3 - 4 = -1$ | $f(3) = 4 - 3 = 1$ | $(-1, 1)$ | A |
| 4 | 6 | $f(7) = 5 - 3 = 2$ | $f(4) = 3 - 6 = -3$ | $(2, -3)$ | B |
| 5 | 2 | $f(8) = 3 - 7 = -4$ | $f(5) = 7 - 2 = 5$ | $(-4, 5)$ | A |
| 6 | 4 | $f(9) = 7 - 3 = 4$ | $f(6) = 3 - 4 = -1$ | $(4, -1)$ | B |
| 7 | 3 | $f(10) = W_{13} - 5 = *$ | $f(7) = 5 - 3 = 2$ | $(*, *)$ | A |
| 8 | 7 | $f(11) = W_{14} - 3 = *$ | $f(8) = 3 - 7 = -4$ | $(*, *)$ | B |
| 9 | 3 | $f(12) = W_{15} - 7 = *$ | $f(9) = 7 - 3 = 4$ | $(*, *)$ | A |
| 10 | 5 | $f(13) = W_{16} - W_{13} = *$ | $f(10) = W_{13} - 5 = *$ | $(*, *)$ | B |
| 11 | 3 | $f(14) = W_{17} - W_{14} = *$ | $f(11) = W_{14} - 3 = *$ | $(*, *)$ | A |
| 12 | 7 | $f(15) = W_{18} - W_{15} = *$ | $f(12) = W_{15} - 7 = *$ | $(*, *)$ | B |

Figure 14:
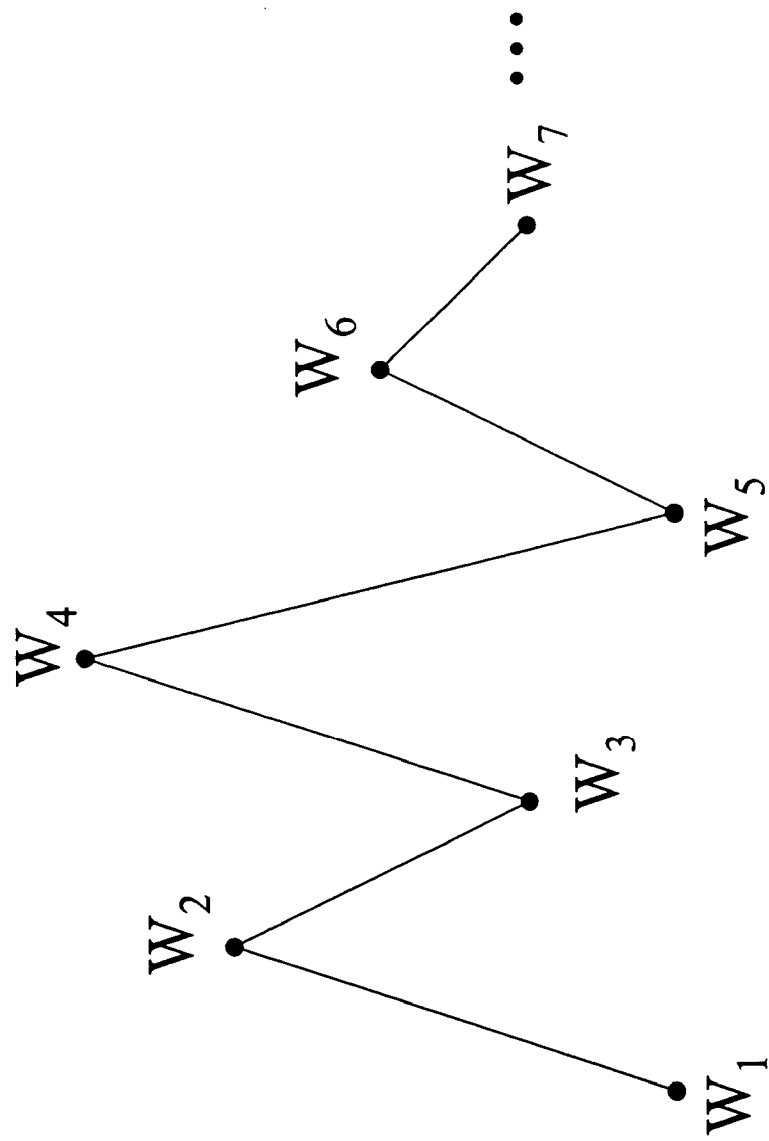
FIG. 14 illustrates a plot of values of data corresponding to values representative of a morphology feature.

FIG. 14 illustrates a plot of the feature values from Tables 1–3 for beat-one $B_1$ through beat-seven $B_7$ where each peak and each valley of the plot can represent a respective feature value W (e.g., value-one $W_1$ which represents beat-one $B_1$, value-two $W_2$ which represents beat-two $B_2$, . . . , value-seven $W_7$ which represents beat-seven $B_7$).

Figure 15:
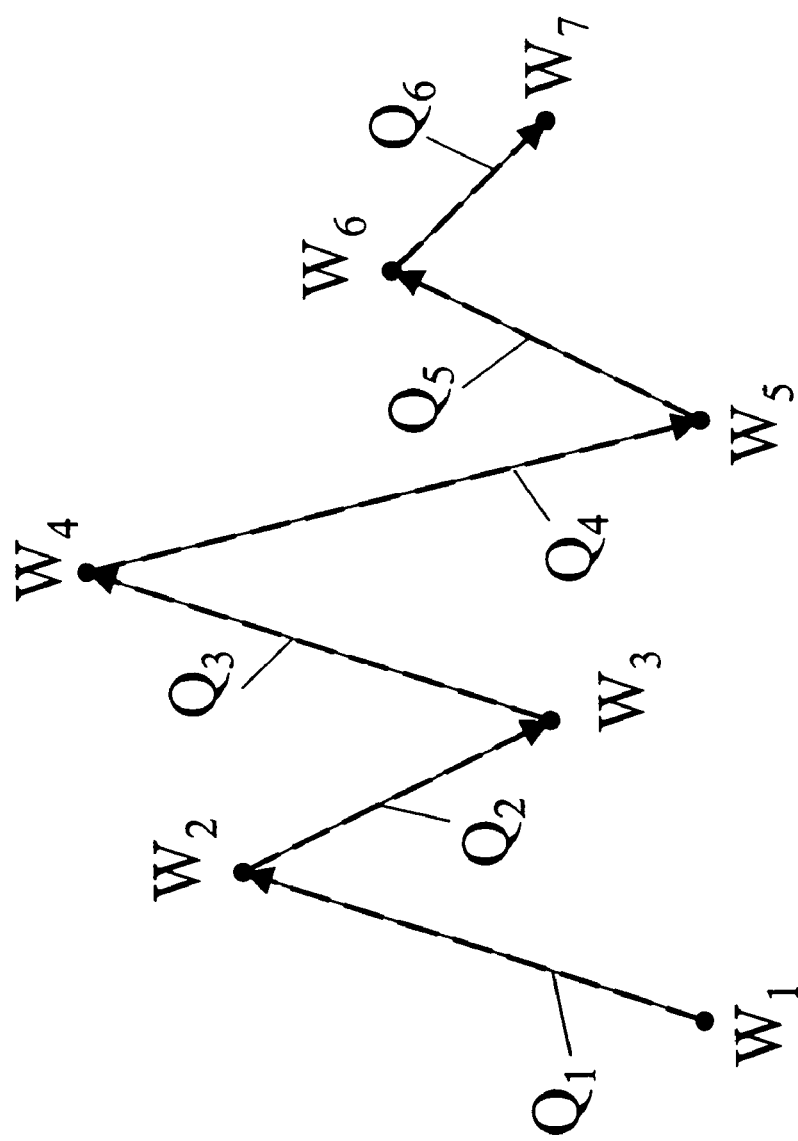
FIG. 15 illustrates a determination of difference features using the values plotted in FIG. 14.

FIG. 15 illustrates for [N]=1 how the mathematical functions Feature(beat+[N]) and Feature(beat) determine the first and second values of the points L which represent the difference features $Q_K$ and $Q_{K+1}$. For [N]=1, the seven values (i.e., value-one $W_1$ through value-seven $W_7$) generate six difference features (i.e., difference feature-one $Q_1$ through difference feature-six $Q_6$). Referring to Table 1, the first mathematical function generates difference feature-two $Q_2$ through difference feature-six $Q_6$ for beat-one $B_1$ through beat-five $B_5$, respectively, using the seven values, and the second mathematical function generates difference feature-one $Q_1$ through difference feature-six $Q_6$ for beat-one $B_1$ through beat-six $B_6$, respectively, using the seven values.

The difference feature Q is illustrated in FIG. 15 as dotted-line arrows extending between two specified values of the plot of FIG. 14. As an example, to determine difference feature-three $Q_3$ (i.e., the first value of the point L as determined by the first mathematical function Feature(beat+[N]) for beat-two $B_2$, the second value of the point L as determined by the second mathematical function Feature(beat) for beat-three $B_3$), the difference can be found between value-four $W_4$ which represents beat-four $B_4$ and value-three $W_3$ which represents beat-three $B_3$. Similarly, to determine difference feature-six $Q_6$ (i.e., the first value of the point L as determined by the first mathematical function Feature(beat+[N]) for beat-two $B_5$, the second value of the point L as determined by the second mathematical function Feature(beat) for beat-six $B_6$), the difference can be found between value-four $W_7$ which represents beat-seven $B_7$ and value-six $W_6$ which represents beat-six $B_6$.

Figure 16:
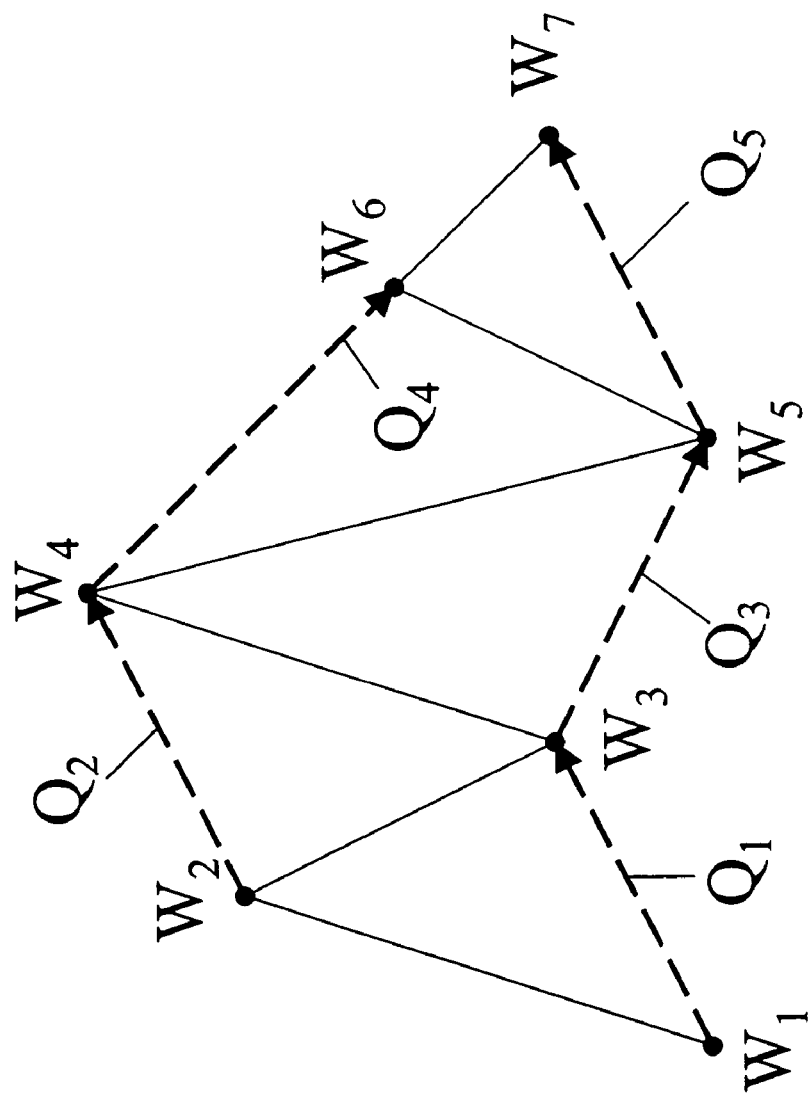
FIG. 16 illustrates another determination of difference features using the values plotted in FIG. 14.

FIG. 16 illustrates for [N]=2 how the mathematical functions Feature(beat+[N]) and Feature(beat) determine the first and second values of the points L which represent the difference features $Q_K$ and $Q_{K+2}$. For [N]=2, the seven values (i.e., value-one $W_1$ through value-seven $W_7$) generate five difference features (i.e., difference feature-one $Q_1$ through difference feature-five $Q_5$). Referring to Table 2, the first mathematical function generates difference feature-three $Q_3$ through difference feature-five $Q_5$ for beat-one $B_1$ through beat-three $B_3$, respectively, using the seven values, and the second mathematical function generates difference feature-one $Q_1$ through difference feature-five $Q_5$ for beat-one $B_1$ through beat-five $B_5$, respectively, using the seven values.

The difference feature Q is illustrated in FIG. 16 as dotted-line arrows extending between two specified values of the plot of FIG. 14. As an example, to determine difference feature-three $Q_3$ (i.e., the first value of the point L as determined by the first mathematical function Feature(beat+[N]) for beat-one $B_1$, the second value of the point L as determined by the second mathematical function Feature(beat) for beat-three $B_3$), the difference can be found between value-five $W_5$ which represents beat-five $B_5$ and value-three $W_3$ which represents beat-three $B_3$. Similarly, to determine difference feature-five $Q_5$ (i.e., the first value of the point L as determined by the first mathematical function Feature(beat+[N]) for beat-three $B_3$, the second value of the point L as determined by the second mathematical function Feature(beat) for beat-five $B_5$), the difference can be found between value-four $W_7$ which represents beat-seven $B_7$ and value-five $W_5$ which represents beat-five $B_5$.

Figure 17:
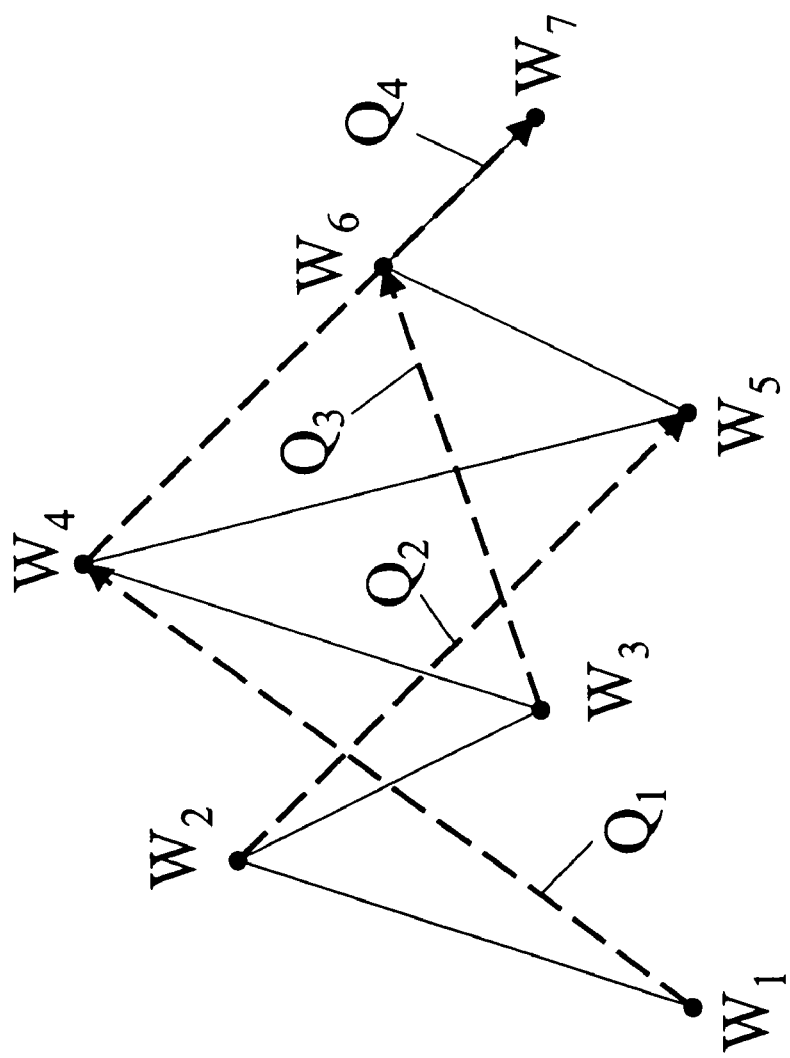
FIG. 17 illustrates a further determination of a difference feature using the values plotted in FIG. 14.

FIG. 17 illustrates for [N]=3 how the mathematical functions Feature(beat+[N]) and Feature(beat) determine the first and second values of the points L which represent the difference features $Q_K$ and $Q_{K+3}$. For [N]=3, the seven values (i.e., value-one $W_1$ through value-seven $W_7$) generate four difference features (i.e., difference feature-one $Q_1$ through difference feature-four $Q_4$). Referring to Table 3, the first mathematical function generates difference feature-four $Q_4$ for beat-four $B_4$ using the seven values, and the second mathematical function generates difference feature-one $Q_1$ through difference feature-four $Q_4$ for beat-one $B_1$ through beat-four $B_4$, respectively, using the seven values.

The difference feature Q is illustrated in FIG. 17 as dotted-line arrows extending between two specified values of the plot of FIG. 14. As an example, to determine difference feature-three $Q_4$ (i.e., the first value of the point L as determined by the first mathematical function Feature(beat+[N]) for beat-one $B_1$, the second value of the point L as determined by the second mathematical function Feature(beat) for beat-three $B_3$), the difference can be found between value-seven $W_7$ which represents beat-seven $B_7$ and value-four $W_4$ which represents beat-four $B_4$.

As shown by the "Group" column of Tables 1–3, each point L can be assigned to a respective group (e.g., group A or group B). The points L representing each odd beat (e.g., beat-one $B_1$, beat-three $B_3$, . . . , beat-eleven $B_{11}$) can be assigned to a first group (i.e., group A), and the points representing each even beat (e.g., beat-two $B_2$, beat-four $B_4$, . . . , beat-twelve $B_{12}$) can be assigned to a second group (i.e., group B). The points L can be assigned to group A and group B in this manner to represent a proposed odd-even alternans pattern of variation (i.e., ABAB . . . ). In other embodiments, the points L can be alternatively assigned to groups to represent other proposed alternans patterns of variation (e.g., AABBAABB . . . , AABAAB . . . , and the like).

As shown in FIG. 3, the processor can plot (at 110) a feature map [e.g., a feature map of Feature(beat+[N]) versus Feature(beat)]. Both groups of points L (e.g., group A and group B) can be plotted on the same axis to generate the feature map. The polarity of the differences of the group A points are inverted relative to the polarities of the differences of the group B points. As a result, plotting the points L determined using the mathematical functions Feature(beat) and Feature(beat+[N]) as defined by Equations 1 and 2 can accentuate any difference between the values specified by the mathematical functions Feature(beat) and Feature(beat+[N]). The inverted polarity of the differences between the first and second groups is illustrated in FIGS. 15–17 where the direction of the dotted-line arrows that represent the difference features Q alternates between adjacent difference features Q.

Figure 20:
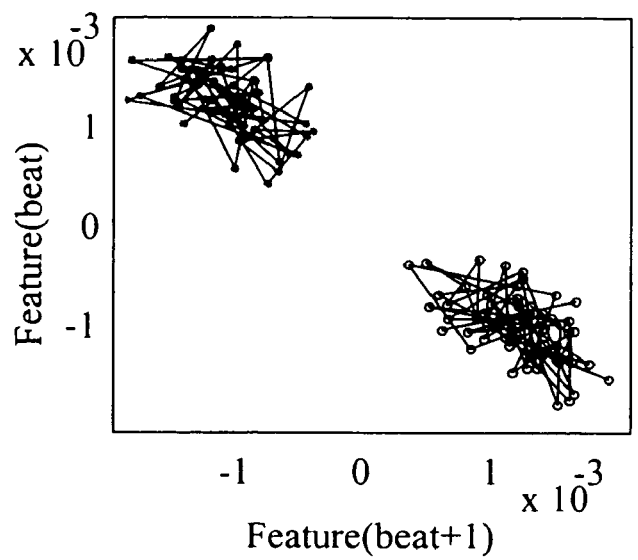
FIG. 20 illustrates a feature map of first and second groups of points generated using a first mathematical function and a second mathematical function.
Figure 21:
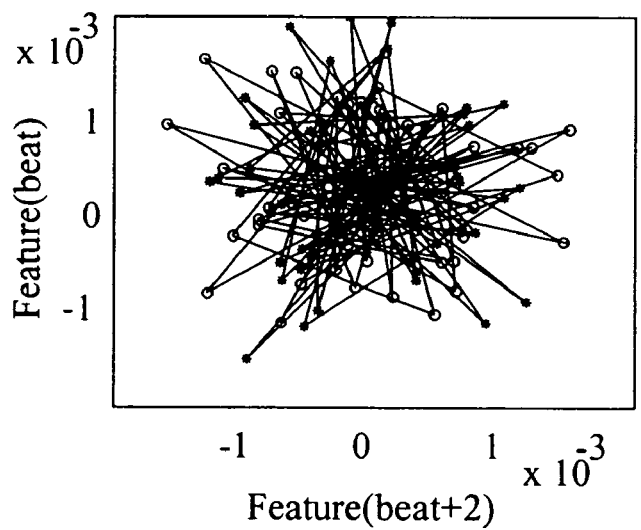
FIG. 21 illustrates a feature map of third and fourth groups of points generated using a third mathematical function and a fourth mathematical function.
Figure 22:
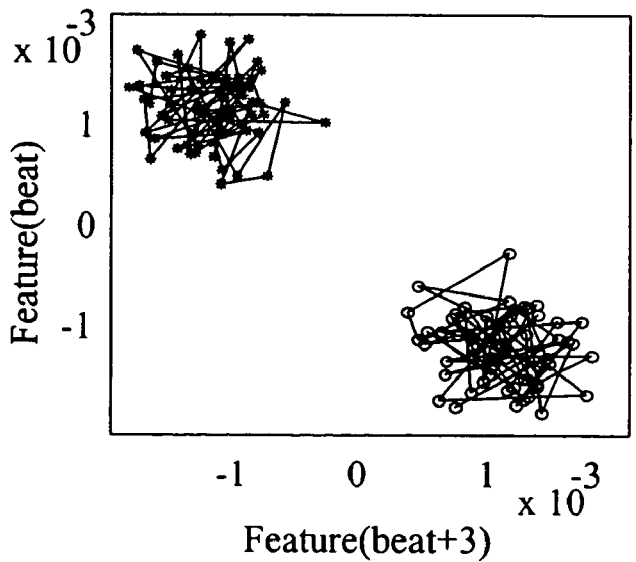
FIG. 22 illustrates a feature map of fifth and sixth groups of points generated using a fifth mathematical function and the sixth mathematical function.

The feature map provides a visual indication of the divergence of the two groups of points, and thus the existence of a significant alternans pattern of variation. If there is a significant ABAB . . . alternans pattern of variation, the two groups of points will show separate clusters on the feature map (for example, as shown in FIGS. 20 and 22). If there is not a significant ABAB . . . alternans pattern of variation, the feature map will illustrate a more random pattern of points from the two groups (for example, as shown in FIG. 21).

Figure 18:
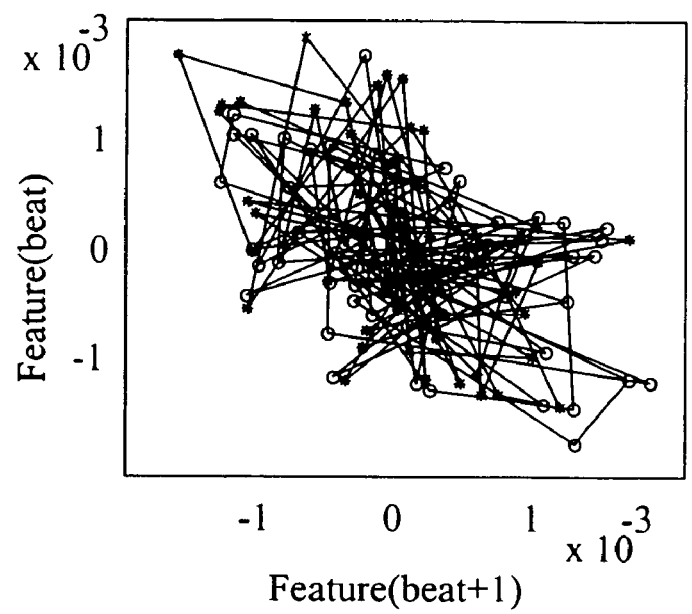
FIG. 18 illustrates a feature map of first and second groups of points generated using values of a vector of data.
Figure 19:
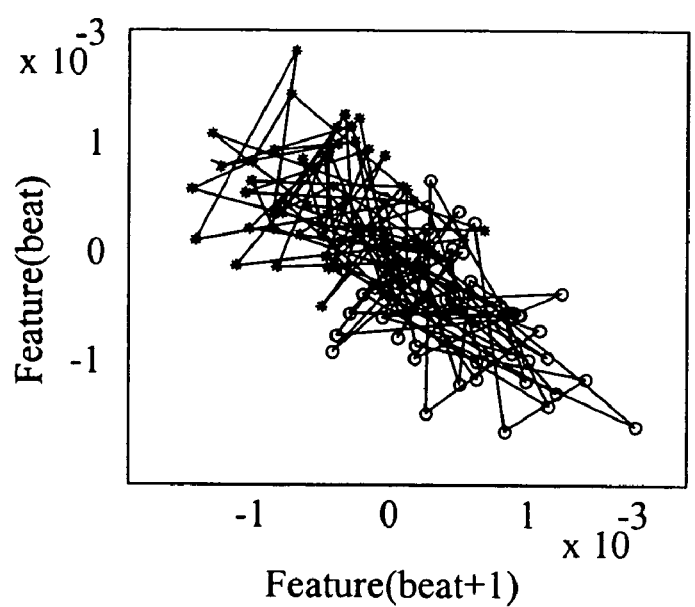
FIG. 19 illustrates a feature map generated using values of a vector of data generated by performing a principal component analysis on a feature matrix including the vector of data utilized to generate the feature map of FIG. 18.

FIGS. 18 and 19 illustrate two examples of feature maps. The [E] points plotted to generate the feature maps of FIGS. 18 and 19 were determined using ECG data representative of an ECG signal having a 5 microvolt TWA pattern of variation, 20 microvolts of noise, and 20 milliseconds of offset, where [H] is equal to 128. The first and second groups of points can be distinguished by the markers utilized to represent the points of the group (i.e., the first group of points, group A, can include asterisks shaped markers, and the second group of points, group B, can include round markers). Lines can be used to connect sequential markers of each group (e.g., for group A, point-two $P_{2A}$ can be connected to each of point-one PIA and point-three $P_{3A}$ by lines).

The feature map of FIG. 18 illustrates a plot of points determined using values directly from the feature matrix A (i.e., the feature matrix A was not preprocessed using a principal component analysis or other mathematical analysis). As illustrated in FIG. 18, the points of the first and second groups are intermixed (i.e., the feature map illustrates a random pattern of the points from the two groups).

Accordingly, the feature map of FIG. 18 does not illustrate the presence of a significant divergence of the two groups of points, and thus, does not indicate the existence of a significant alternans pattern of variation.

The feature map of FIG. 19 illustrates a plot of points determined using values of a first principal vector $u_1$. The first principal vector $u_1$ is a result of a principal component analysis performed on the same feature matrix A from which the values used to determine the points L plotted in FIG. 18 were obtained. As illustrated in FIG. 19, although the first and second groups of points are partially overlapped, the first group of points is primarily positioned in the upper-left quadrant of the feature map and the second group of points is primarily positioned in the lower-right quadrant of the feature map. Accordingly, the feature map of FIG. 19 appears to illustrate the presence of a significant divergence of the two groups of points, and thus, a significant alternans pattern of variation may exist.

Although FIGS. 18 and 19 illustrate the same ECG data, the feature map of FIG. 19 indicates the existence of an alternans pattern of variation, while the feature map of FIG. 18 does not. The effect of noise and time shift in the measured ECG signal on the determined alternans data is clearly indicated by the feature maps of FIGS. 18 and 19. Preprocessing the feature matrix A increases the robustness of the determination of alternans data by limiting the effect of noise and time shift in the measured ECG signal.

In some embodiments, multiple feature maps can be generated for various quantities of [N] using the same set of values (e.g., the feature maps for [N]=1, 2, and 3, respectively, can be generated using the points determined in Tables 1–3). The display of multiple feature maps can further verify the existence of a significant alternans pattern of variation for the proposed alternans pattern of variation (e.g., a ABAB . . . alternans pattern of variation).

FIGS. 20–22 illustrate feature maps for [N]=1, 2, and 3, respectively, where the points plotted in each of the feature maps were determined using the same set of values. The divergence of the first and second groups of points in the feature maps of FIGS. 20 and 22 in combination with the lack of divergence of the first and second groups of points in the feature map of FIG. 21 provides visual evidence that the proposed ABAB . . . alternans pattern of variation is correct.

The operator can change the proposed alternans pattern of variation (i.e., change the grouping of the points to a different alternans pattern of variation) if the feature maps for [N]=1, 2, and 3 do illustrate differing divergence patterns for [N]=1 and 3 and [N]=2, respectively. For example, if the two groups of points diverge in the feature map for [N]=1 and 2, but not for the feature maps of [N]=3, the ECG signal represented by the values used to determine the points for the feature maps does not represent the proposed ABAB . . . alternans pattern of variation. However, the ECG signal can include a different alternans pattern of variation. Reassignment of the [E] points to different groups can be used to test a different proposed alternans pattern of variation.

As shown in FIG. 3, the processor (at 112) can statistically analyze the data plotted in the feature map. Although the feature map provides a visual indication of the existence of a significant alternans pattern of variation, the feature map does not provide a quantitative measure of the confidence level of the alternans pattern of variation. Accordingly, the data plotted in the feature map, or similar types of data that are not plotted in a feature map, can be statistically analyzed to provide such quantitative measures of the confidence level of the alternans pattern of variation.

In some embodiments, a paired T-test can be performed on the first and second groups of points. A paired T-test is a statistical test which is performed to determine if there is a statistically significant difference between two means. The paired T-test can provide a p-value (e.g., p=0.001). In one embodiment, the confidence level is increased (i.e., a significant alternans pattern of variation exists) when the p-value is less than 0.001. In other embodiments, other suitable threshold levels can be established.

In some embodiments, a cluster analysis (e.g., a fuzzy cluster analysis or a K-mean cluster analysis) can be performed on the [E] points to determine a first cluster of points and a second cluster of points. The cluster analysis can also generate a first center point for the first cluster and a second center point for the second cluster. The first and second clusters of points can be compared with the first and second groups of points, respectively. A determination can be made of the number of clustered points that match the corresponding grouped points. For example, if point-one $L_1$ and point-two $L_2$ are clustered in the first cluster, point-three $L_3$ and point-four $L_4$ are clustered in the second cluster, point-one $L_1$, point-two $L_2$, and point-three $L_3$ can be grouped in the first group, and point-four $L_4$ can be grouped in the second group. Clustered point-three $L_3$ does not correspond to grouped point-three $L_3$, thereby resulting in a 75% confidence level. The confidence level can represent the percentage of clustered points that match the corresponding grouped points. In one embodiment, a confidence level about 90% can be a high confidence level, a confidence level between 60% and 90% can be a medium confidence level, and a confidence level below 60% can be a low confidence level. In other embodiments, the thresholds for the high, medium, and/or low confidence levels can be other suitable ranges of percentages or values.

As shown in FIG. 3, the processor can determine (at 114) an estimate of an amplitude of the alternans pattern of variation. As discussed above, in one embodiment, the square-root of a principal component (e.g., the first principal component $S_1$) can be used to provide an estimate of the amplitude. In other embodiments, a distance can be determined between a first center point of a first group of points and a second center point of a second group of points. The center points can include the center points of the first and second groups of points A and B as determined using a mathematical analysis (e.g., by taking the mean or median of the values of the points for each respective group), the center points provided by the Paired T-test, the center points provided by the cluster analysis, or any other determined center points that represent the ECG data.

Figure 23:
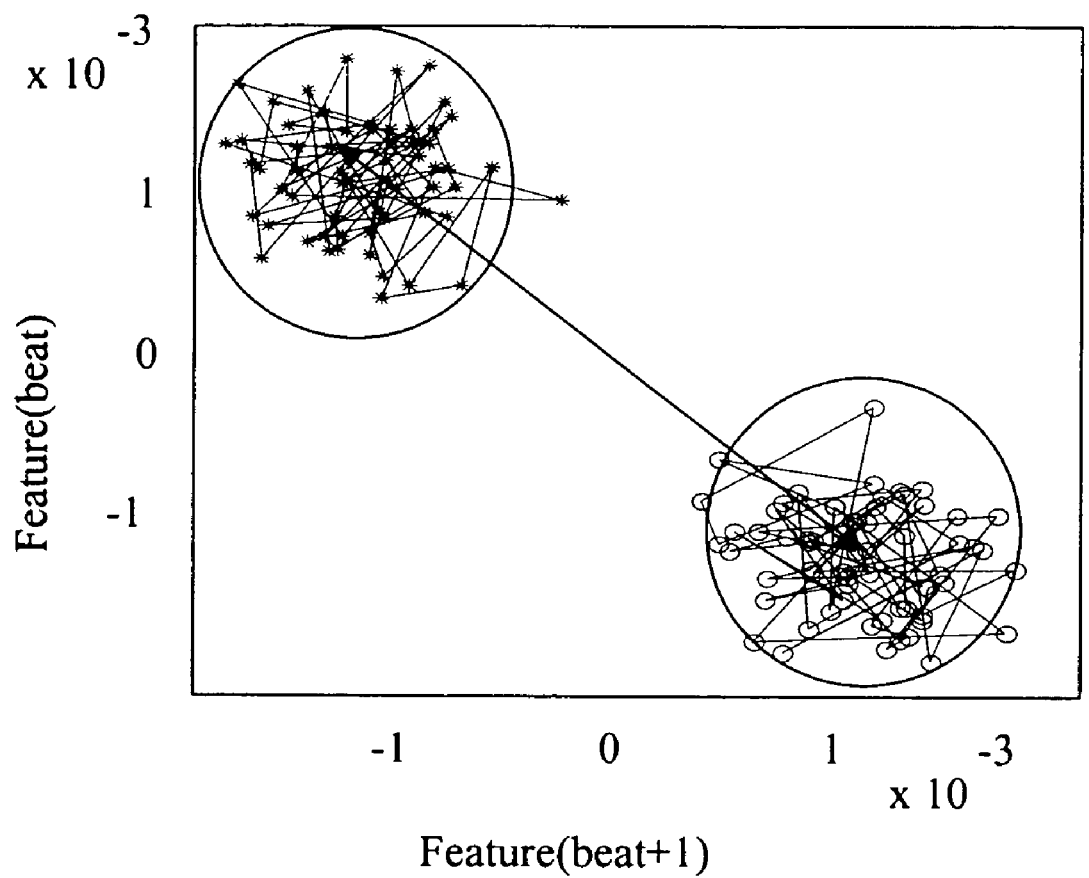
FIG. 23 illustrates a distance between a first center point of a first group of points and a second center point of a second group of points each plotted to form a feature map.

FIG. 23 illustrates a distance measurement between the first and second center points. The distance can be determined using Equation 9 shown below, where the first center point includes an X-value $X_1$ and a Y-value $Y_1$ and the second center point includes an X-value $X_2$ and a Y-value $Y_2$.

$$\text{Amplitude}_{ESTIMATE} = \sqrt{(X_1-X_2)^2+(Y_1-Y_2)^2} \quad [e9]$$

The amplitude of the alternans pattern of variation often depends on the [D] morphology features used to determine the values W. Accordingly, the estimated amplitude is generally not an absolute value that can be compared against standardized charts. However, comparisons can be generated for estimated amplitudes of alternans patterns of variation based on the morphology features F that are determined and the processing step that is used.

As shown in FIG. 3, the processor can report (at 116) alternans data to a caregiver and/or the processor can store the alternans data. The alternans data (e.g., the feature maps, the estimated amplitudes of the alternans pattern of variation, the confidence level of the alternans pattern of variation, the uncertainty level of the alternans pattern of variation, the p-value of the alternans pattern of variation, and the like) can be reported using any suitable means (e.g., output to a suitable output device such as a display, a printer, and the like).

Figure 24:
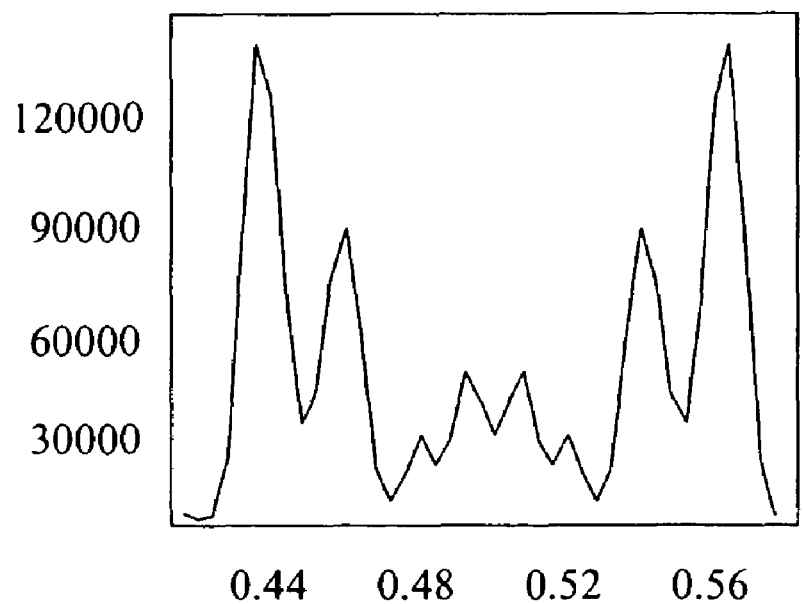
FIG. 24 illustrates a spectral graph generated using values of a vector of data.
Figure 25:
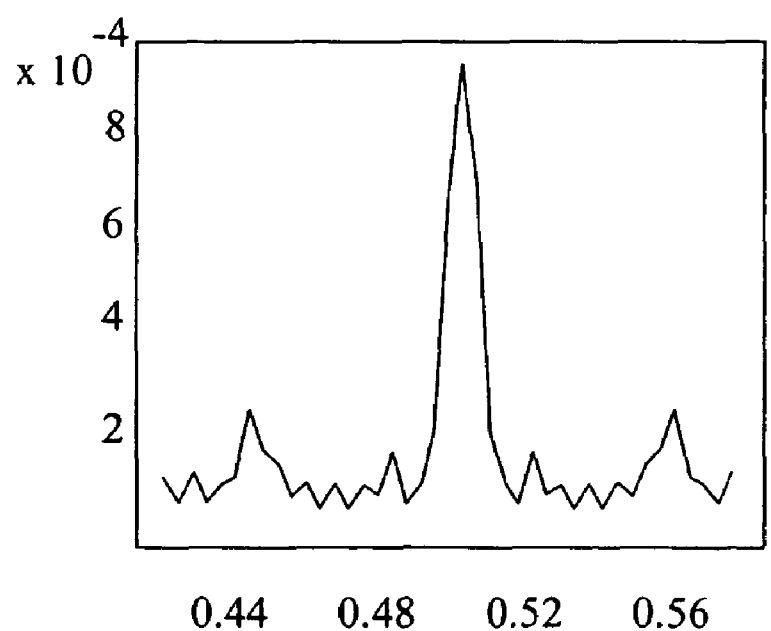
FIG. 25 illustrates a spectral graph generated using values of a vector of data generated by performing a principal component analysis on a feature matrix including the vector of data utilized to generate the spectral graph of FIG. 24.

As shown in FIG. 3, in some embodiments, the processor can plot (at 118) a spectral graph using values resulting from preprocessing the feature matrix (e.g., the values of the first principal component vector $u_1$). FIGS. 24 and 25 illustrate two examples of spectral graphs. The values used to generate the spectral graphs of both FIGS. 24 and 25 were determined using ECG data representative of an ECG signal having a 5 microvolt TWA pattern of variation, 20 microvolts of noise, and 20 milliseconds of offset, where [H] is equal to 128.

FIG. 24 illustrates a spectral graph generated using values directly from the feature matrix A (i.e., the feature matrix A was not preprocessed using a principal component analysis or other mathematical analysis). As illustrated in FIG. 24, the spectral graph does not include a dominant frequency at half of the beat sample frequency, but instead includes a number of frequency spikes having varying amplitudes. Accordingly, the spectral graph of FIG. 24 does not indicate the existence of a significant alternans pattern of variation. FIG. 25 illustrates a spectral graph generated using values of a first principal vector $u_1$. The first principal vector $u_1$ is a result of a principal component analysis performed on the same feature matrix A from which the values used to generate the spectral graph of FIG. 24 were obtained. FIG. 25 illustrates a single frequency spike at half of the beat sample frequency. Accordingly, unlike the spectral graph of FIG. 24, the spectral graph of FIG. 25 appears to illustrate the presence of a significant alternans pattern of variation. The effect of noise and time shift in the measured ECG signal on the determined alternans data is indicated by the spectral graphs of FIGS. 24 and 25. Preprocessing the feature matrix A increases the robustness of the determination of alternans data when using spectral domain methods.

The invention claimed is:

1. A method of determining alternans data of an ECG signal, the method comprising:
    determining at least one value representing at least one morphology feature of each beat of the ECG signal;
    generating a set of data points based on a total quantity of values and a total quantity of beats, the data points each including a first value determined using a first mathematical function and a second value determined using a second mathematical function;
    separating the data points into a first group of points and a second group of points;
    generating a feature map by plotting the first group of points and the second group of points in order to assess an alternans pattern of variation; and
    determining an estimated amplitude of the alternans pattern of variation by determining a first center point and a second center point of the data points and determining a distance between the first center and the second center point.

2. A method as set forth in claim 1 and further comprising assigning the data points representing an odd beat to the first group of points and assigning the data points representing an even beat to the second group of points.

3. A method as set forth in claim 1 and further comprising:
    generating a feature matrix based on the total quantity of values and the total number of beats; and
    processing the feature matrix using a principal component analysis,
    the principal component analysis generating principal component vectors and principal components,
    the data points corresponding to at least one of the principal component vectors.

4. A method as set forth in claim 3 and further comprising determining an estimated amplitude of the alternans pattern of variation by calculating a square-root of at least one of the principal components.

5. A method as set forth in claim 1 and further comprising using the feature map to visually determine whether an alternans pattern of variation exists.

6. A method as set forth in claim 5 wherein an alternans pattern of variation exists if the first group of points are spaced from the second group of points and an alternans pattern of variation does not exist if the first group of points are not spaced from the second group of points.

7. A method as set forth in claim 1 wherein the first mathematical function and the second mathematical function each calculate a difference feature.

8. A method as set forth in claim 1 and further comprising:
    generating a second set of data points, the data points of the second set including a third value determined using a third mathematical function and a fourth value determined using a fourth mathematical function;
    separating the data points of the second set into a third group of points and a fourth group of points; and
    generating a second feature map by plotting the third group of points and the fourth group of points.

9. A method as set forth in claim 8 and further comprising:
    generating a third set of data points, the data points of the third set including a fifth value determined using a fifth mathematical function and a sixth value determined using a sixth mathematical function;
    separating the data points of the third set into a fifth group of points and a sixth group of points; and
    generating a third feature map by plotting the fifth group of points and the sixth group of points.

10. A method as set forth in claim 9 and further comprising comparing the feature map, the second feature map, and the third feature map to assess an alternans pattern of variation.

11. A method as set forth in claim 1 and further comprising:
    processing the data points using a cluster analysis, the cluster analysis generating a first cluster of points and a second cluster of points;
    comparing the first cluster of points with the first group of points;
    comparing the second cluster of points with the second group of points; and
    determining a value representative of matched points between the first cluster of points and the first group of points and matched points between the second cluster of points and the second group of points.

12. A method as set forth in claim 1 and further comprising assessing T-wave alternans data of the ECG signal.

13. A method as set forth in claim 1 and further comprising determining at least one value representing at least one non-amplitude-based morphology feature.

14. A device for determining alternans data of an ECG signal, the device comprising:

means for determining at least one value representing at least one morphology feature of each beat of the ECG signal;

means for generating a set of data points based on a total quantity of values and a total quantity of beats, the data points each including a first value determined using a first mathematical function and a second value determined using a second mathematical function;

means for separating the data points into a first group of points and a second group of points; and means for generating a feature map by plotting the first group of points and the second group of points in order to assess an alternans pattern of variations wherein the feature map is used to visually determine whether an alternans, pattern of variation exists, such that an alternans pattern of variation exists if the first group of points are spaced from the second group of points and an alternans pattern of variation does not exist if the first group of points are not spaced from the second group of points.

15. A method of determining alternans data of an ECG signal, the method comprising:

determining at least one value representing at least one morphology feature of each beat of the ECG signal;

generating a set of data points based on a total quantity of values and a total quantity of beats, the data points each including a first value determined using a first mathematical function and a second value determined using a second mathematical function;

separating the data points into a first group of points and a second group of points;

generating a feature map by plotting the first group of points and the second group of points in order to assess an alternans pattern of variation;

processing the data points using a cluster analysis, the cluster analysis generating a first cluster of points and a second cluster of points;

comparing the first cluster of points with the first group of points;

comparing the second cluster of points with the second group of points; and determining a value representative of match points between the first cluster of points and the first group of points and matched point between the second cluster of points and the second group of points.

\* \* \* \* \*